(12) United States Patent
Winger et al.

(10) Patent No.: US 11,685,911 B2
(45) Date of Patent: Jun. 27, 2023

(54) FUNGAL POLYPEPTIDES HAVING LYSOZYME ACTIVITY

(71) Applicant: MONAGHAN MUSHROOMS GROUP, Tyholland (IE)

(72) Inventors: Alison Marie Winger, Cloyne (IE); Ciaran Forde, County Cork (IE); Anne McMeel, County Monaghan (IE); Andrew Dowd, County Monaghan (IE); Gabriele Gucciardo, Lurgan (GB)

(73) Assignee: MONAGHAN MUSHROOM S GROUP, Tyholland (IE)

( * ) Notice: Subject to any disclaimer, the term of this patent is extended or adjusted under 35 U.S.C. 154(b) by 728 days.

(21) Appl. No.: 15/999,451

(22) PCT Filed: Feb. 16, 2017

(86) PCT No.: PCT/EP2017/053547
§ 371 (c)(1),
(2) Date: Aug. 16, 2018

(87) PCT Pub. No.: WO2017/140807
PCT Pub. Date: Aug. 24, 2017

(65) Prior Publication Data
US 2021/0032614 A1    Feb. 4, 2021

(30) Foreign Application Priority Data
Feb. 16, 2016 (DK) .............................. PA201670085

(51) Int. Cl.
| | | |
|---|---|---|
| C12N 9/36 | (2006.01) | |
| A23K 20/147 | (2016.01) | |
| A23K 30/00 | (2016.01) | |
| A23K 10/14 | (2016.01) | |
| A23L 29/00 | (2016.01) | |
| A23L 33/18 | (2016.01) | |
| A23L 3/3571 | (2006.01) | |
| A61K 8/66 | (2006.01) | |
| A61Q 11/00 | (2006.01) | |
| A61Q 19/10 | (2006.01) | |
| A61K 38/00 | (2006.01) | |

(52) U.S. Cl.
CPC ............ *C12N 9/2462* (2013.01); *A23K 10/14* (2016.05); *A23K 20/147* (2016.05); *A23K 30/00* (2016.05); *A23L 3/3571* (2013.01); *A23L 29/06* (2016.08); *A23L 33/18* (2016.08); *A61K 8/66* (2013.01); *A61Q 11/00* (2013.01); *A61Q 19/10* (2013.01); *C12Y 302/01017* (2013.01); *A23V 2002/00* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,355,022 | A | 10/1982 | Rabussay |
| 5,223,409 | A | 6/1993 | Ladner et al. |
| 6,395,966 | B1 | 5/2002 | Mumm et al. |
| 7,151,204 | B2 | 12/2006 | Houmard et al. |

FOREIGN PATENT DOCUMENTS

| | | | | |
|---|---|---|---|---|
| EP | 0238023 | B2 | 10/2002 | |
| EP | 1718742 | B1 | 12/2014 | |
| WO | 91/14772 | A1 | 10/1991 | |
| WO | 92/06204 | A1 | 4/1992 | |
| WO | 95/17413 | A1 | 6/1995 | |
| WO | 95/22625 | A1 | 8/1995 | |
| WO | 95/33836 | A1 | 12/1995 | |
| WO | 96/00787 | A1 | 1/1996 | |
| WO | 00/21381 | A1 | 4/2000 | |
| WO | 00/24883 | A1 | 5/2000 | |
| WO | 00/56900 | A2 | 9/2000 | |
| WO | 2004/017988 | A1 | 3/2004 | |
| WO | 2004/026334 | A1 | 4/2004 | |
| WO | 2005011587 | A2 | 2/2005 | |
| WO | 2005/080559 | A1 | 9/2005 | |
| WO | 2005/100573 | A2 | 10/2005 | |
| WO | 2006/092396 | A1 | 9/2006 | |
| WO | 2008/098933 | A1 | 8/2008 | |
| WO | 2008/124764 | A1 | 10/2008 | |
| WO | 2009/106703 | A2 | 9/2009 | |
| WO | 2013/076253 | A1 | 5/2013 | |
| WO | 2013076259 | A2 | 5/2013 | |
| WO | WO-2014202616 | A2 | * 12/2014 | ............. C07K 14/37 |

OTHER PUBLICATIONS

Houbraken J et al. Rasmsonia, a new genus comprising thermotolerant and thermophilic Talaromyces and Geosmithia species. 2012. Antonie van Leeuwenhoek. 101:403-421 (copy mailed on Oct. 15, 2021).*

Felch, James, W., et al., "The N, O-diacetylmuramidase of *Chalaropsis* species. V. The complete amino acid sequence", The Journal of Biological Chemistry, vol. 250, No. 10, May 25, 1975, pp. 3713-3720.

International Search Report received for International Patent Application No. PCT/EP2017/053547, dated Apr. 11, 2017, 5 pages.

International Preliminary Report on Patentability and Written Opinion received for International Patent Application No. PCT/EP2017/053547, dated Aug. 21, 2018, 6 pages.

Nagi Waba et al., From the Departments of Microbiology and Biochemistry, Vanderbilt University School of Medicine, Nashville,Tennessee 37232 published "The N, O-Diacetylmuramidase of *Chalaropsis* Species, IV. The Tryptic peptides" in the Journal of Biological Chemistry in vol. 250, No. 10, Issued on May 25, 1975, pp. 3709-3712.

(Continued)

*Primary Examiner* — Paul J Holland
(74) *Attorney, Agent, or Firm* — Greer, Burns & Crain, Ltd.

(57) ABSTRACT

Novel lysozyme enzymes from the genus of *Rasamsonia*.

23 Claims, 5 Drawing Sheets

Figure 1:
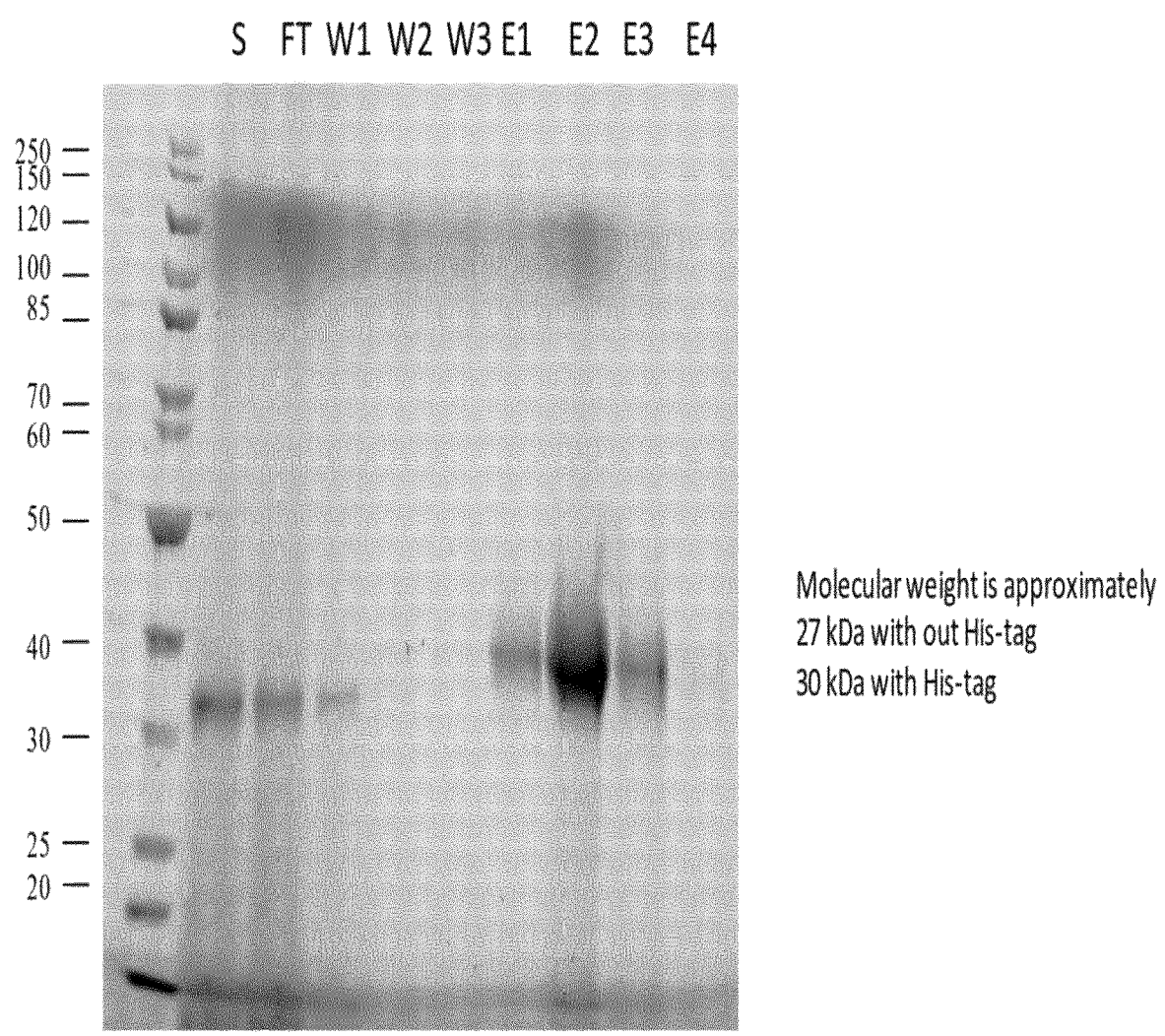

Specification includes a Sequence Listing.

(56) References Cited

OTHER PUBLICATIONS

Shelly J Rasmussen-Wilson et al., from MycoTox, Inc., Denver, Colorado 80262, published "Expression of a Plant Protein by Neurospora crassa" in Applied and Environmental Microbiology, vol. 63, No. 9, in Sep. 1997, pp. 3488-3493.

G. Kohler et al., issued "Continuous cultures of fused cells secreting antibody of predefined specificity" in Nature vol. 256, on Aug. 7, 1975, pp. 495-497.

Albert Hinnen et al., From Department of Botany, Genetics and Development, Cornell University, Ithaca, New York 14853, published "Transformation of yeast (gene exchange/hybrid plasmid/integration)" in Proc. Natl. Acad. Sci. USA, vol. 75, No. 4, in Apr. 1978, Genetics pp. 1929-1933.

A. Franck et al., from Laboratoire de Viroiogie, Institut de Biologie Moleculaire et Cellulaire du CNRS,15 rue Descartes, 67084 Strasbourg Cbdex, France published "Nucleotide Sequence of Cauliflower Mosaic Virus DNA" in Cell, vol. 21, in Aug. 1980, Copyright@1980 by MIT, pp. 285-294.

Hisao Ito et al., from Research Institute for Food Science, Kyoto University, Kyoto 611, Japan, published "Transformation of Intact Yeast Cells Treated with Alkali Cations" in Journal of Bacteriology, vol. 153, No. 1, in Jan. 1983, pp. 163-168.

M. Melanie Yelton et al., from Department of Plant Pathology, University of California, Davis, CA 95616, published "Transformation of Aspergillus nidulans by Using a trpC Plasmid (hybrid plasmid/gene transfer/chromosome integration)" in Proceedings of the National Academy of Sciences, USA, vol. 81, on Mar. 1984, Genetics, 6 pages, pp. 1470-1474.

Keith M. Derbyshire et al., from Department of Molecular Biophysics and Biochemistry, Yale University, New Haven, CT 06510 (U.S.A) published "A simple and efficient procedure for saturation mutagenesis using mixed oligodeoxynucleotides (Recombinant DNA; cloning single-stranded DNA; site-directed mutagenesis)" in Gene 46, Elsevier, in 1986, pp. 145-152.

Dan Eaton et al. from Department of Protein Biochemistry, Genentech, Inc., South San Francisco, California 94080, published "Proteolytic Processing of Human Factor VIII. Correlation of Specific Cleavages by Thrombin, Factor Xa, and Activated Protein C with Activation and Inactivation of Factor VIII Coagulant Activity" in Biochemistry 25(2), on Jan. 28, 1986, pp. 505-512.

V. L. Hughey et al., from Food Research Institute, University of Wisconsin, Madison, Wisconsin 53706, published "Antimicrobial Activity of Lysozyme against Bacteria Involved in Food Spoilage and Food-Borne Disease" in Applied and Environmental Microbiology, vol. 53, No. 9, in Sep. 1987, pp. 2165-2170.

D.Cullen et al. from USDA Forest Products Laboratory, Madison, WI, USA published "Sequence and centromere proximal location of a transformation enhancing fragment ansl from Aspergillus nidulans" in vol. 15, No. 22, on Nov. 25, 1987, pp. 9163-9175.

Sarbjit S. Ner et al., published "A Simple and Efficient Procedure for Generating Random Point Mutations and for Codon Replacements Using Mixed Oligodeoxynucleotides" in DNA, vol. 7, No. 2, in Mar. 1988, pp. 127-134.

Tove Christensen et al., from Novo Research Institute, DK2880 Bagsvaerd, Denmark, published "High Level Expression of Recombinant Genes in Aspergillus Oryzae" in Biotechnology vol. 6, in Dec. 1988, pp. 1419-1422.

Paul Carter et al., from Genentech, Znc., 460 Point San Bruno Boulevard, South San Francisco, California 94080, published "Engineering Subtilisin BPN' for Site-Specific Proteolysis" in Protein: Structure, Function, and Genetics 6,in 1989, pp. 240-248.

Laurence Malardier et al., published "Cloning of the nitrate reductase gene (niaD) of Aspergillus nidulans and its use for transformation of Fusarium oxysporum (Chlorate resistance; gene library; heterologous gene expression; phytopathogenic fungus; recombinant DNA)" in Elsevier, vol. 78, Issue 1, on May 15, 1989, pp. 147-156.

Ko Shimamoto et al, from Plantech Research Institute, 1000 Kamoshida, Midori-ku, Yokohama, 227, Japan, published "Fertile transgenic rice plants regenerated from transformed protoplasts" in Nature 338, vol. 338, on Mar. 16, 1989, pp. 274-276.

Charles S. Gasser et al.', from University of California, published "Genetically Engineering Plants for Crop Improvement" in Science, New Series, vol. 244, No. 4910, on Jun. 16, 1989 by American Association for the Advancement of Science, pp. 1293-1299.

James U. Bowie et al., Department of Biology, Massachusetts Institute of Technology, Cambridge, MA 02139, published "Identifying determinants of folding and activity for a protein of unknown structure" in Proc. Nati. Acad. Sci. USA, vol. 86, in Apr. 1989, pp. 2152-2156.

Janice W. Edwards et al., from The Laboratory of Plant Molecular Biology, The Rockefeller University, New York, New York 10021-6399, published "Cell-Specific Gene Expression in Plants" in Annu. Rev. Genet, vol. 24, in Dec. 1990, pp. 275-303.

Ingo Potrykus from Institute for Plant Sciences, Swiss Federal Institute of Technology (ETH), ETH Zentrum, CH-8092 Zurich, Switzerland, published "Gene Transfer to Cereals: An Assessment" in Biotechnology, on Jun. 1, 1990, pp. 535-542.

Robert I.Lehrer et al., from West Los Angeles VA Hospital, Los Angeles, CA 90073, U.S.A. published "Ultrasensitive assays for endogenous antimicrobial polypeptides" in Journal of Immunological Methods, 137 on Mar. 21, 1991, pp. 167-173.

Wanggen Zhang et al., from Cornell University, Ithaca, New York 14853 published "Analysis of Rice Act1 5' Region Activity in Transgenic Rice Plants" in The Plant Cell, vol. 3, in Nov. 1991, pp. 1155-1165.

David Gems et al., from Institute qf Genetics, University of Glasgow, Glasgow, Scotland (U.K), published "An autonomously replicating plasmid transforms Aspergillus nidufans at high frequency (Transformation; recombinant DNA; plasmid stability; inverted repeat)" in Elsevier vol. 98, Issue 1, on Feb. 1, 1991, pp. 61-67.

Clark F. Ford et al., from University of Turku, Turku, Finland, published "Fusion Tails for the Recovery and Purification of Recombinant Proteins" in Protein Expression and Purification, vol. 2, Issues 2-3, in Apr.-Jun. 1991, pp. 95-107.

Henry B. Lowman et al., from Department of Protein Engineering, Genentech, Inc., 460 Point San Bruno Boulevard, South San Francisco, California 94080, published "Selecting High-Affinity Binding Proteins by Monovalent Phage Display" in Biochemistry on Nov. 12, 1991, pp. 10832-10838.

Paul J.J. Hooykaas et al., from Clusius Laboratory, Institute of Molecular Plant Sciences, Leiden University, Wassenaarseweg 64, 2333, AL Leiden, Netherlands, published "Agrobacterium and plant genetic engineering" in Plant Molecular Biology, 19, in May 1992, pp. 15-38.

Alexander Wlodaver et al., from Macromolucar Structure Laboratory, NCI-Fredrick Cancer Research and Development Center, MD 21702, published "Crystal structure of human recombinant interleukin-4 at 2.25 A resolution" in Elsevier, vol. 309, No. 1, in Aug. 1992, pp. 59-64.

Michael A. Romanos et al., from Department of Cell Biology, Wellcome Research Laboratories. Beckenham, Kent BR3 3BS, U.K. published "Foreign Gene Expression in Yeast: a Review" in Yeast vol. 8, in Jun. 1992, pp. 423-488.

Paul Christou, published "Genetic transformation of crop plants using microprojectile bombardment" in The Plant Journal 2(3), in Feb. 1992, pp. 275-281.

Vimla Vasil et al., published "Herbicide Resistant Fertile Transgenic Wheat Plants Obtained by Microprojectile Bombardment of Regenerable Embryogenic Callus" in BioTechnology, 10(6), on Jun. 1, 1992, pp. 667-674.

Alan H. Christensen et al., published "Maize polyubiquitin genes: structure, thermal perturbation of expression and transcript splicing, and promoter activity following transfer to protoplasts by electroporation" in Plant Molecular Biology 18, in Feb. 1992, pp. 675-689.

Lorna J. Smith et al., from Inorganic Chemistry Laboratory, University of Oxford, England. published "Human Interleukin 4 The Solution Structure of a Four-helix Bundle Protein" in J Mol Biol. vol. 224, Issue 4, on Apr. 20, 1992, pp. 899-904.

Serik Omirulleh et al., published "Activity of a chimeric promoter with the doubled CaMV 35S enhancer element in protoplast-derived cells and transgenic plants in maize" in Plant Molecular Biology 21, in Feb. 1993, pp. 415-428.

(56) References Cited

OTHER PUBLICATIONS

Soichiro Nakamura et al., from the Department of Biochemistry, Yamuguchi University, Yamaguchi 753 and the Department of Food and Nutrition, Ube College, Yamaguchi 755, Japan, published "Hyperglycosylation of Hen Egg White Lysozyme in Yeast" in Journal of Biological Chemistry, vol. 268, No. 17, on Jul. 1993, pp. 12706-12712.

Junko Kyozuka et al., from Plantech Research Institute, Yokohama, Japan, published "Light-regulated and cell-specific expression of tomato rbcS-gusA and rice rbcS-gusA fusion genes in transgenic rice" in Plant Physiol, vol. 102(3), in Jul. 1993, pp. 991-1000.

Antony A.Cooper et al., from Institute of Molecular Biology, University of Oregon, Eugene, OR 97403, USA, published "Protein splicing of the yeast TFP1 intervening protein sequence: a model for self-excision" in The EMBO Journal vol. 12 No. 6, on Jun. 1993, pp. 2575-2583.

Deping Xu et al., from Field of Botany, Cornell University, Ithaca, NY 14853., published "Systemic induction of a potato pin2 promoter by wounding, methyl jasmonate, and abscisic acid in transgenic rice plants" in Plant Molecular Biology, vol. 22, on Jul. 1993, pp. 573-588.

Tipton KF. published "Nomenclature Committee of the International Union of Biochemistry and Molecular Biology (NC-IUBMB). Enzyme Nomenclature. Recommendations 1992. Supplement 4: corrections and additions (1994)" in Eur J Biochem, vol. 223(1), on Jul. 1, 1994, pp. 1-5.

Ko Shimamoto from Plantech Research Institute, Yokohama, Japan, published "Gene expression in transgenic monocots" in Elsevier, Current Opinion in Biotechnology, vol. 5, Issue 2, in Apr. 1994, pp. 158-162.

Masaki Ito et al., from Nagoya University BioScience Center, Japan, published "Meristem-specific gene expression directed by the promoter of the S-phase-specific gene, cyc07, in transgenic *Arabidopsis*" in Plant Molecular Biology, vol. 24, in Mar. 1994, pp. 863-878.

Amitava Mitra et al., from Department of Plant Pathology and The Center for Biotechnology, University of Nebraska, Lincoln, NE 68583-0722, USA published "The Chlorella virus adenine methyltransferase gene promoter is a strong promoter in plants" in Plant Molecular Biology, vol. 26, in Oct. 1994, pp. 85-93.

Zijian Guo et al., from Department of Biochemistry, University of Rochester School of Medicine and Dentistry, Rochester, New York 14642, published "3'-End-Forming Signals of Yeast mRNA" in Molecular and Cellular Biology, vol. 15, No. 11, in Nov. 1995, pp. 5983-5990.

Alan J, Barrett. from The Babraham Institute.Cambridge, England, published "Nomenclature Committee of the International Union of Biochemistry and Molecular Biology (NC-IUBMB). Enzyme Nomenclature. Recommendations 1992. Supplement 2: corrections and additions (1994)" in Eur J Biochem, vol. 232, in Aug. 1995, pp. 1-6.

Lisa A. Collins-Racie et al., from Genetics Institute, Inc., 87 Cambridge Park Drive, Cambridge, ,MA 02140, published "Production of Recombinant Bovine Enterokinase Catalytic Subunit in *Escherichia coli* Using the Novel Secretory Fusion Partner DsbA" in Biotechnology, vol. 13, on Sep. 1, 1995, pp. 982-987.

Pauline P.Ward et al., from Department of Cell Biology, Baylor College of Medicine, Houston, TX 77030, USA, published "A system for production of commercial quantities of human lactoferrin: a broad spectrum natural antibiotic" in Biotechnology (NY), vol. 13, in May 1995, pp. 498-503.

Yasuaki Kagaya et al., from Institute for Cell Biology and Genetics, Faculty of Agriculture, Iwate University, Japan, published "The promoter from the rice nuclear gene encoding chloroplast aldolase confers mesophyll-specific and light-regulated expression in transgenic tobacco" in Mol Gen Genet, vol. 248, on Oct. 25, 1995, pp. 668-674.

Alan J, Barrett. from The Babraham Institute.Cambridge, CB2 4AT, England, published "Nomenclature Committee of the International Union of Biochemistry and Molecular Biology (NC-IUBMB). Enzyme Nomenclature. Recommendations 1992. Supplement 3: corrections and additions (1995)" in Eur J Biochem, vol. 237, in Apr. 1996, pp. 1-5.

Douglas J. Hilton et al., from Whitehead Institute for Biomedical Research, Cambridge, Massachusetts 02142, USA, published "Saturation mutagenesis of the WSXWS motif of the erythropoietin receptor" in the Journal of Biological Chemistry, vol. 271, No. 9, on Mar. 1, 1996, pp. 4699-4708.

Alan J, Barrett. from The Babraham Institute.Cambridge, CB2 4AT, England, published "Nomenclature Committee of the International Union of Biochemistry and Molecular Biology (NC-IUBMB). Enzyme Nomenclature. Recommendations 1992. Supplement 4: corrections and additions (1997)" in Eur J Biochem, vol. 250, in Nov. 15, 1997, pp. 1-6.

Udo Conrad et al., published "High-level and stable accumulation of single-chain Fv antibodies in plant storage organs" in Journal of Plant Physiology, vol. 152, Issue 6, in Jun. 1998, pp. 708-711.

Emily C.F. Chen et al., from Graduate Institute of Agricultural Biotechnology, National Chung-Hsing University, Taichung, Taiwan 40227, ROC, published "Identification of Three Novel Unique Proteins in Seed Oil Bodies of Sesame" in Plant cell Physiological vol. 39, Issue 9, in Sep. 1998, pp. 935-941.

Chuan-Yin Wu et al., published "Promoters of Rice Seed Storage Protein Genes Direct Endosperm-Specific Gene Expression in Transgenic Rice" in Plant and Cell Physiology, vol. 39, Issue 8, on Aug. 1, 1998, pp. 885-889.

Jon E. Ness et al., from Maxygen, 3410 Central Expressway, Santa Clara, CA 95051, USA, published "DNA shuffling of subgenomic sequences of subtilisin" in Nature Biotechnology, vol. 17, in Sep. 1999, pp. 893-896.

IUPAC-IUBMB Joint Commission on Biochemical Nomenclature (JCBN) and Nomenclature Committee of IUBMB (NC-IUBMB) Published in Eur. J. Biochem vol. 264, Issue 2, in Sep. 1999, pp. 607-609.

Monika Svetina et al., from National Institute of Chemistry, L-11: Laboratory for Biosynthesis and Biotransformation, Hajdrihova 19, SI-1000 Ljubljana, Slovenia, published "Expression of catalytic subunit of bovine enterokinase in the filamentous fungus *Aspergillus niger*" in Journal of Biotechnology, vol. 76, on Jan. 21, 2000, pp. 245-251.

Daniel Martin et al., from Instituto de Investigaciones Biomédicas and the Departamento de Bioquímica, Facultad de Medicina, Universidad Autonoma de Madrid, 28029 Madrid, Spain, published "Regulation of heme oxygenase-1 expression through the phosphatidylinositol 3 kinase/Akt pathway and the Nrf2 transcription factor in response to the antioxidant phytochemical, carnosol." in JBC Papers in Press, on Dec. 19, 2003,as Manuscript M309660200,47 pages.

Raymond C. Stevens, published "The cost and value of three-dimensional protein structure" in Drug Discovery World Summer 2003, of Main Conference: Sep. 24-25, 2003, pp. 35-48.

Alberto Barbiroli et al., published "Antimicrobial activity of lysozyme and lactoferrin incorporated in cellulose-based food packaging" in Food Control, vol. 26, Issue 2, on Aug. 2012, pp. 387-392.

Mamata Singhvi et al., published "Protoplast Formation and Regeneration in Acetobacter Pasteurianus" in Columbia International Publishing American Journal of Bioengineering and Biotechnology, vol. 1 No. 2, Published online Aug. 3, 2013, pp. 37-43.

Brian C. Cunningham et al., from Department of Biomolecular Chemistry, Genentech, South San Francisco, CA 94080, published "High-resolution epitope mapping of hGH-receptor interactions by alanine-scanning mutagenesis" in Science, New Series, vol. 244, No. 4908, on Jun. 2, 1989, pp. 1081-1085.

John F. Reidhaar-Olson et al., published "Combinatorial Cassette Mutagenesis as a Probe of the Informational Content of Protein Sequences" in Science, New Series, vol. 241, No. 4861, on Jul. 1, 1988, pp. 53-57.

Abraham M. de Vos et al., published "Human Growth Hormone and Extracellular Domain of its Receptor: Crystal Structure of the Complex" in Science, New Series, vol. 255, No. 5042, on Jan. 17, 1992, pp. 306-312.

(56) References Cited

OTHER PUBLICATIONS

Philip E. Dawson et al., published "Synthesis of Proteins by Native Chemical Ligation" in Science, New Series, vol. 266, No. 5186, on Nov. 4, 1994, pp. 776-779.

* cited by examiner

SEQUENCE LISTING

```
<160> NUMBER OF SEQ ID NOS: 6

<210> SEQ ID NO 1
<211> LENGTH: 837
<212> TYPE: DNA
<213> ORGANISM: Talaromyces emersonii - Rasamsonia emersonii
<220> FEATURE:
<221> NAME/KEY: misc_feature
<222> LOCATION: (1)..(54)
<223> OTHER INFORMATION: Encoding signal or propeptide
<220> FEATURE:
<221> NAME/KEY: misc_feature
```

-continued

```
<222> LOCATION: (55)..(837)
<223> OTHER INFORMATION: Encoding mature polypeptide

<400> SEQUENCE: 1
atgtccgttc gtcagcttct cgtggccgga tccctggcca gcctggccaa ggccttgcct     60
ttcccccagc ctggagagat catggacaag ttctatcgag tcctcgaggc cagaaatacc    120
gttgacattc ttgcgagagc gactggggag acggtcacca accccaacct cgccgtctac    180
accgtcaacg actacgatgg aatcggcgcc ggaaccgact cgtacacctt ctacactgga    240
gatggctcga ctgccgctgg ctggcccgac cagtcgcaat gggtctcctt cattgatatg    300
ttcaacaaca acaagaacgc catgttcgcc ggctgcgagc agtacggcgt tgcggacgac    360
agcggccccg aggtaggtag catctggaac gccatcgagc aggtcgccgc cgagacgtac    420
gtcgaccacc gtttcatcct ggctgtcatc atgcaggagt cgaccggctg cgtccgcgcg    480
ccgaccagct acggcgccgt tcccaacccg ggcctgatgc aggaccacga cggatcggcc    540
acttgcaact acggcaacgg caatgtggta accccctgcc gcaagacac catcactcag     600 atggtgagcg aaggaactgc cggtacatcc tccggcgacg gcctggccaa ctgcctgaac    660
tatgctcctg ccggtgccgg cgcccaggcc ttctaccagg ccgcgcggat ctacaactcg    720
ggctcgatcg atcccagcgg tgacctggga aagggtgtcg ctacgcactg ctacgcctcg    780
gacattgcca accgcttgac ctgggtgggtg tcggcgccga ggacctgcac ccttgat     837

<210> SEQ ID NO 2
<211> LENGTH: 279
<212> TYPE: PRT
<213> ORGANISM: Talaromyces emersonii - Rasamsonia emersomii
<220> FEATURE:
<221> NAME/KEY: SIGNAL
<222> LOCATION: (1)..(18)
<220> FEATURE:
<221> NAME/KEY: mat_peptide
<222> LOCATION: (18)..(279)

<400> SEQUENCE: 2

Met Ser Val Arg Gln Leu Leu Val Ala Gly Ser Leu Ala Ser Leu Ala
        -15                 -10                  -5

Lys Ala Leu Pro Phe Pro Gln Pro Gly Glu Ile Met Asp Lys Phe Tyr
 -1   1               5                  10                  15

Arg Val Leu Glu Ala Arg Asn Thr Val Asp Ile Leu Ala Arg Ala Thr
                 20                  25                  30

Gly Glu Thr Val Thr Asn Pro Asn Leu Ala Val Tyr Thr Val Asn Asp
             35                  40                  45

Tyr Asp Gly Ile Gly Ala Gly Thr Asp Ser Tyr Thr Phe Tyr Thr Gly
         50                  55                  60

Asp Gly Ser Thr Ala Ala Gly Trp Pro Asp Gln Ser Gln Trp Val Ser
 65                  70                  75

Phe Ile Asp Met Phe Asn Asn Asn Lys Asn Ala Met Phe Ala Gly Cys
 80                  85                  90                  95

Glu Gln Tyr Gly Val Ala Asp Asp Ser Gly Pro Glu Val Gly Ser Ile
                100                 105                 110

Trp Asn Ala Ile Glu Gln Val Ala Ala Glu Thr Tyr Val Asp His Arg
            115                 120                 125

Phe Ile Leu Ala Val Ile Met Gln Glu Ser Thr Gly Cys Val Arg Ala
        130                 135                 140

Pro Thr Ser Tyr Gly Ala Val Pro Asn Pro Gly Leu Met Gln Asp His
    145                 150                 155
```

```
Asp Gly Ser Ala Thr Cys Asn Tyr Gly Asn Gly Asn Val Val Asn Pro
160                 165                 170                 175

Cys Pro Gln Asp Thr Ile Thr Gln Met Val Ser Glu Gly Thr Ala Gly
            180                 185                 190

Thr Ser Ser Gly Asp Gly Leu Ala Asn Cys Leu Asn Tyr Ala Pro Ala
        195                 200                 205

Gly Ala Gly Ala Gln Ala Phe Tyr Gln Ala Ala Arg Ile Tyr Asn Ser
    210                 215                 220

Gly Ser Ile Asp Pro Ser Gly Asp Leu Gly Lys Gly Val Ala Thr His
    225                 230                 235

Cys Tyr Ala Ser Asp Ile Ala Asn Arg Leu Thr Gly Trp Val Ser Ala
240                 245                 250                 255

Pro Arg Thr Cys Thr Leu Asp
                260

<210> SEQ ID NO 3
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 3
atgtccgttc gtcagcttct                                              20

<210> SEQ ID NO 4
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 4
ctaattgtta tcaagggtgc aggt                                         24

<210> SEQ ID NO 5
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 5
aaaagaattc ttgcctttcc cccagcct                                     28

<210> SEQ ID NO 6
<211> LENGTH: 34
<212> TYPE: DNA
<213> ORGANISM: Artificial Sequence
<220> FEATURE:
<223> OTHER INFORMATION: Primer
```

```
<220> FEATURE:
<221> NAME/KEY: misc_feature
<223> OTHER INFORMATION: Primer

<400> SEQUENCE: 6
aaaaatctag accattgtta tcaagggtgc aggt                               34
```

FUNGAL POLYPEPTIDES HAVING LYSOZYME ACTIVITY

FIELD

The aspects of the disclosed embodiments relate to fungal polypeptides from *Rasamsonia* having lysozyme activity; to nucleic acids encoding the polypeptides; to nucleic acid constructs comprising the coding nucleic acids; to vectors comprising the nucleic acid constructs and to a microbial cells comprising the vectors. The aspects of the disclosed embodiments further relate to methods of producing the polypeptides and their use.

BACKGROUND

Lysozyme is a glycoside hydrolase enzyme generally classified as (EC 3.2.1.17) and also known as muramidase or N-acetylmuramide glycanhydrolase or O-glycosyl hydrolase. Lysozymes catalyzing hydrolysis of 1,4-beta-linkages between N-acetylmuramic acid and N-acetyl-D-glucosamine residues in a peptidoglycan and between N-acetyl-D-glucosamine residues in chitodextrins. The antimicrobial mechanism of lysozyme is different from the lactams, and many bacteria have been observed to have difficulties developing resistance towards Lysozyme. Therefore, Lysozyme is useful for killing highly resistant bacteria, for example methicillin-resistant or vancomycin-intermediate staphylococci.

Lysozyme enzymes are produced by some organisms, including higher mammals such as humans, as defense against bacteria and can be found in secretes, such as nasal secretions, intestinal fluids, urine, tears, saliva, human milk, and mucus and in the cytoplasmic granules of macrophages and polymorphonuclear neutrophils. Lysozyme is particularly abundant in egg white. Lysozymes antibacterial properties is provided by its ability to attack peptidoglycans (found in the cell walls of bacteria, especially Gram-positive bacteria) and hydrolyzing the glycosidic bond that connects N-acetylmuramic acid with the fourth carbon atom of N-acetylglucosamine. Hydrolyzing these linkages lysozyme damages the bacterial cell wall thereby enabling osmotic lysis of the bacterium.

Lysozyme can be classified into five different glycoside hydrolase (GH) classes (CAZy, www.cazy.org): GH22 (hen egg-white lysozyme), GH23 (goose egg-white lysozyme), GH24 (bacteriophage T4 lysozyme), GH73 (*Sphingomonas* flagellar protein) and GH25 (*Chalaropsis* lysozymes).

Industrial application of egg white lysozyme is known for example in cheese production. Here the egg white lysozyme has been found to be effective in destroying vegetative forms of Clostridia bacteria and specifically *Clostridium tyrobutyricum*. These bacteria tends to survive pasteurization and heat treatments in cheese production and they may later propagate to cause late blowing during cheese maturation.

Another example of industrial application of egg white lysozyme is known from pharmacology where egg white lysozyme contained in pharmaceutical preparations is promoted against bacterial infection.

However, lysozyme from different sources display different specificities against different bacteria and therefore there is a continuous demand for providing new lysozyme enzymes providing new specificities against bacteria. For example hen egg white lysozyme which is the primary product available on the commercial market, does not cleave N,6-0-diacetylmuramidase in e.g. *Streptococcus aureus* cell walls and is thus not effective against this important human pathogen among others.

In addition to a demand for new lysozyme variants having improved activity properties such as new bacterial specificities, there is also a demand for improved ways of producing such new lysozyme, preferably in a simple and cost effective manner.

One such way of manufacture would be to express lysozyme in a microbial host in a fermentation. A suitable host would naturally not include bacteria having cell walls, sensitive to degradation by the lysozyme. Therefore, the inventors of the present invention found that fungal hosts may be a preferable host. However, due to both technical challenges in cross genus heterologous expression and also a general desire to avoid producing the lysozyme in a host which would be labelled Genetically Modified Organisms (GMO) the present inventors set out to identify a lysozyme of fungal origin, particularly one which could be readily produced in a host known to be an industrial expression providing good yields.

However, only few lysozymes of fungal origin are known in the art such as the GH25 lysozyme from *Chalaropsis* disclosed in Felsch J W, Ingagami T, and Hash J H. (1975) *The N,0-Diacetylmuramidase of Chalaropsis species; V The complete amino acid sequence. JBC.* 250:10 pp 3713-3720) or WO2005/011587.

Other examples of fungal lysozymes are the GH25 lysozyme from *Trametes cinnabaria* disclosed in EP 171874261, the lysozyme from *Acremonioum alkalophilum* disclosed in WO2013/076253, the lysozyme from *Aspergillus aculeatus* disclosed in WO2013/076259 or the lysozyme from *Trichoderma reesei* of WO2009/106703.

SUMMARY

The inventors of the present disclosure have unexpectedly identified, isolated and characterized a new lysozyme polypeptide from the fungal species *Rasamsonia emersonii*. This is the first time lysozyme has been found in a *Rasamsonia* genus and it is indeed a surprise to find lysozyme in a *Rasamsonia* since the entire genome of a *Rasamsonia emersonii* strain, disclosed in WO 2014/202616 did not reveal any lysozyme polypeptides. Further the sequence of this lysozyme is very remote from the sequence of any of the few known fungal lysozymes.

Accordingly, the present disclosure provides in a first aspect a lysozyme enzyme from *Rasamsonia*.

In a further aspect, the present disclosure provides a lysozyme enzyme from *Rasamsonia emersonii*.

In a still further, aspect the present disclosure provides a polynucleotide encoding polypeptides of the invention.

In a still further aspect, the present disclosure provides a nucleic acid construct comprising the polynucleotide of the invention and wherein the polynucleotide is operably linked to one or more control sequences which direct the expression of a polypeptide from the polynucleotide in a microbial cell harboring the nucleic acid construct.

In a still further aspect, the present disclosure provides an expression vector comprising the polynucleotide of the invention, a promoter sequence and transcriptional and translational stop signals.

In a still further aspect, the present disclosure provides a host cell comprising the polypeptide of the invention, the polynucleotide of the invention and/or the nucleic acid construct and/or vector of the present disclosure.

In a still further aspect, the present disclosure provides a transgenic plant, plant part or plant cell comprising the polypeptide of the invention, the polynucleotide of the present disclosure and/or the nucleic acid construct and/or vector of the present disclosure.

In a still further aspect, the present disclosure provides a composition comprising the polypeptide and/or the host cell of the invention.

In a still further aspect, the present disclosure provides a method for preparing a polypeptide of the invention comprising cultivating a cell of the invention under condition allowing the cell to express the polypeptide and, optionally, recovering the expressed polypeptide.

In a still further aspect, the present disclosure provides a method for preparing host cells of the present disclosure, comprising selecting one or more host cells of the invention and propagating them under conditions suitable for the host cells to multiply and, optionally, isolating the host cells.

In a still further aspect, the present disclosure provides a non-therapeutic use of a polypeptide of the invention for treating a peptidoglycan or chitodextrin substrate or for killing or inhibiting a microorganism.

In a still further aspect, the present disclosure provides a polypeptide or a composition of the present disclosure for killing or inhibiting a microorganism on or in the human or animal body.

In a still further aspect, the present disclosure provides a method for treating a peptidoglycan or chitodextrin substrate comprising contacting said substrate with a polypeptide of the present disclosure.

In a still further aspect, the present disclosure provides a method for killing or inhibiting a microorganism comprising contacting said substrate with a polypeptide of the present disclosure.

In a still further aspect, the present disclosure provides an antibody capable of binding to one or more epitopes of the polypeptide of the polypeptide.

In a still further aspect, the present disclosure provides a method for detecting the presence of a polypeptide comprising providing a sample suspected of containing the polypeptide, contacting the sample with the antibody of the present disclosure, and detecting if binding between the antibody and a polypeptide in the sample has occurred.

In a still further aspect, the present disclosure provides a method for detecting the presence of an antibody comprising providing a sample suspected of containing the antibody, contacting the sample with the polypeptide of the present disclosure, and detecting if binding between the polypeptide and the antibody in the sample has occurred.

In a still further aspect, the present disclosure provides a kit for detecting a polypeptide of the invention comprising a sample container, means for introducing an antibody of the present disclosure to the sample, and means for detecting binding of the antibody to the polypeptide in the sample.

In a still further aspect, the present disclosure provides a kit for detecting an antibody of the present disclosure comprising a sample container, means for introducing a polypeptide of the invention to the sample, and means for detecting binding of the antibody to the polypeptide in the sample.

In a still further aspect, the present disclosure provides a method for reducing immunogenicity of a polypeptide of the invention comprising binding one or more PEG moieties to the polypeptide of the present disclosure.

DESCRIPTION OF DRAWINGS AND FIGURES

FIG. 1: SDS gel of his tagged an non his tagged polypeptide of the invention

Figure 2:
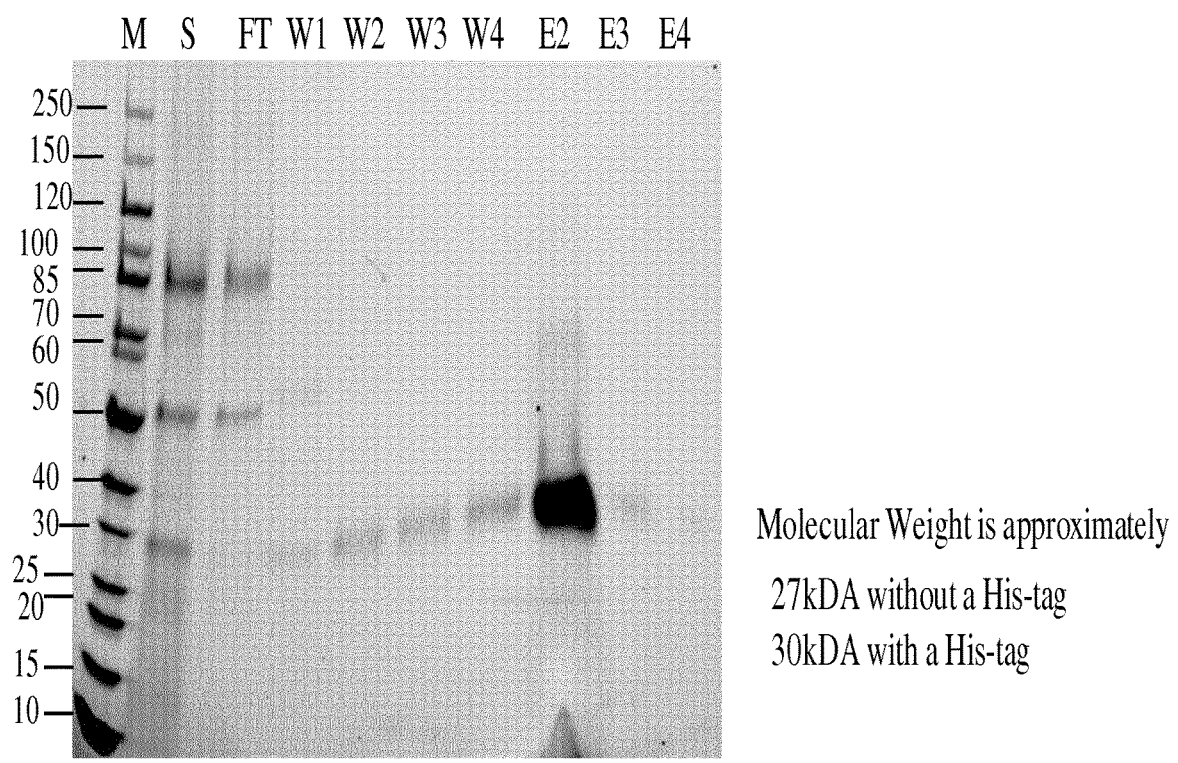

FIG. 2: Lysozyme activity of the polypeptide of the invention.

Figure 3:
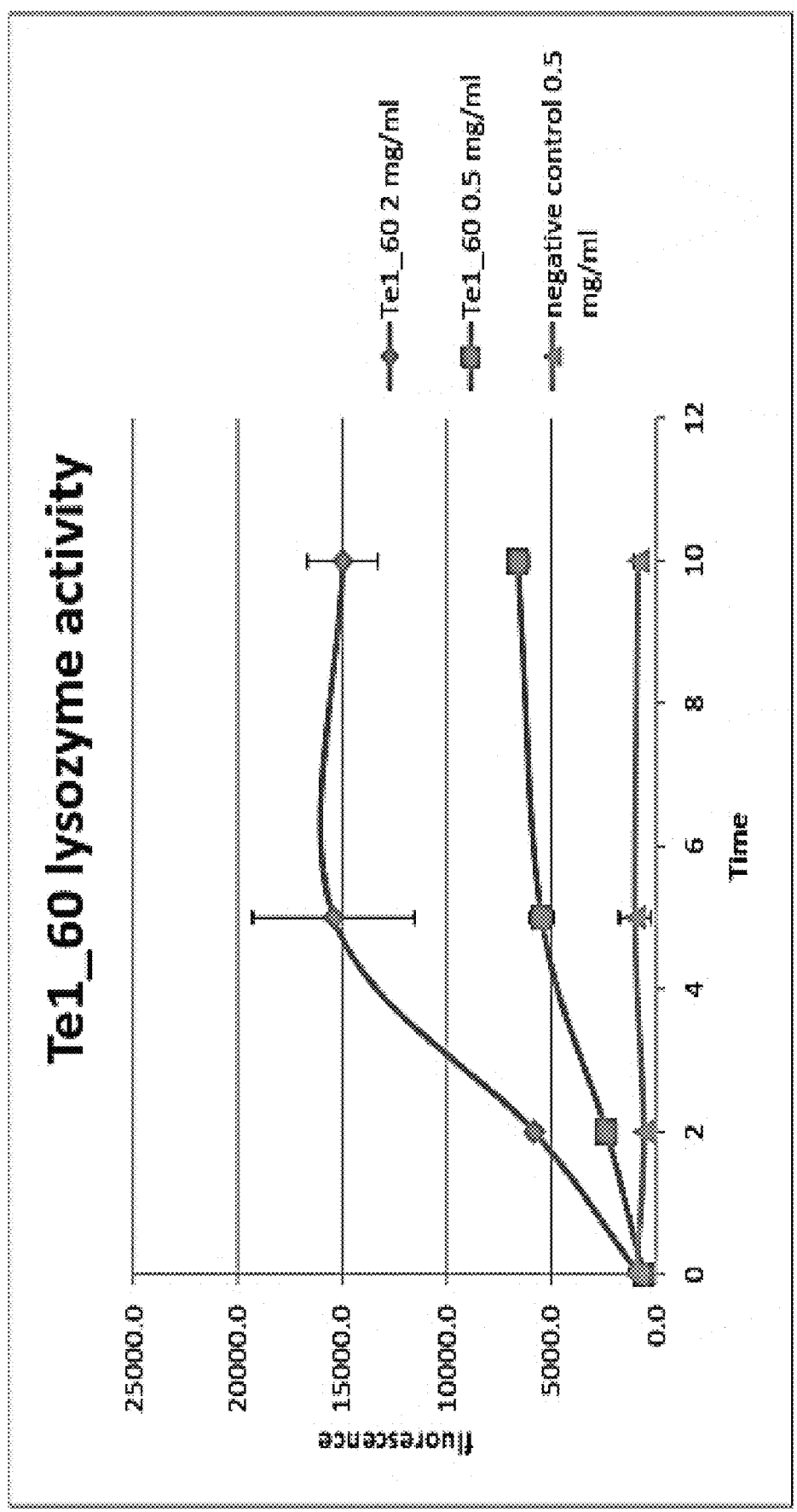

FIG. 3: Lysozyme activity of SEQ ID NO: 2

Figure 4:
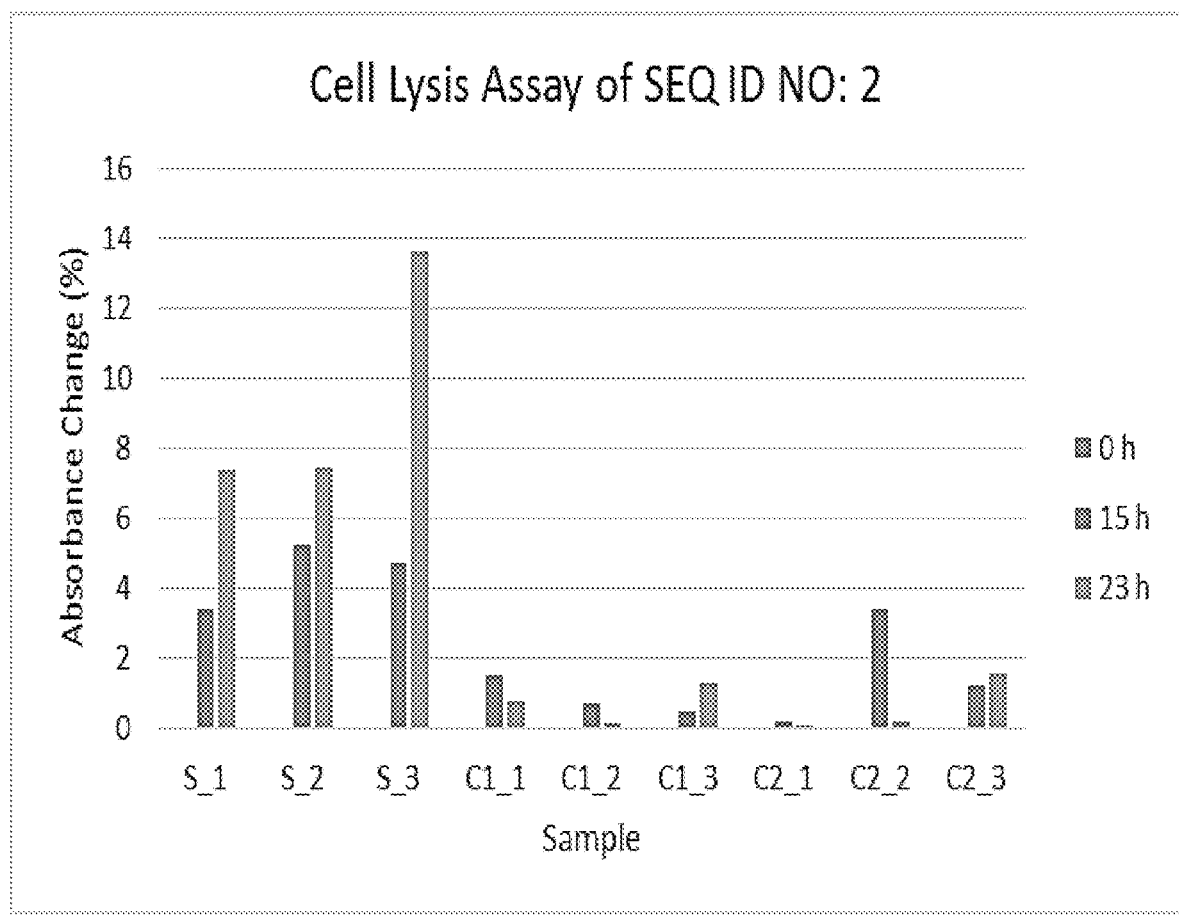

FIG. 4: Cell Lysis activity of SEQ ID NO: 2

Figure 5:
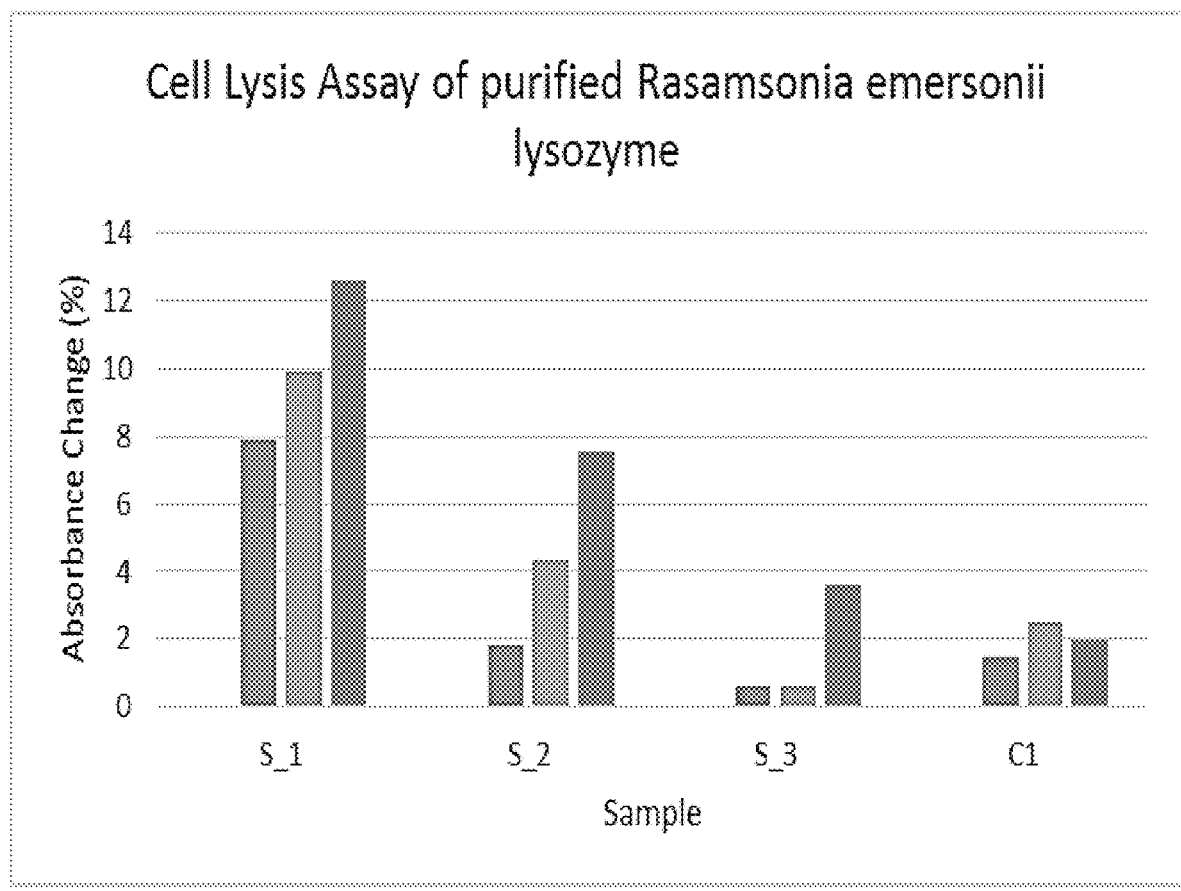

FIG. 5: Cell Lysis activity of *Rasamsonia emersonii* lysozyme purified from culture media

REFERENCE TO SEQUENCE LISTING

This application contains a sequence listing in computer readable form, which is incorporated herein by reference.
SEQ ID NO:1:
cDNA sequence encoding lysozyme polypeptide of the invention.
SEQ ID NO:2:
Amino acid sequence for lysozyme polypeptide of the invention.
SEQ ID NO:3:
Primer DNA sequence
SEQ ID NO:4:
Primer DNA sequence
SEQ ID NO:5:
Primer DNA sequence
SEQ ID NO:6:
Primer DNA sequence

DETAILED DESCRIPTION

This section disclose detailed embodiments of the present disclosure.

Definitions

The EC numbers used herein refers to Enzyme Nomenclature 1992 from NC-IUBMB, Academic Press, San Diego, Calif., including 30 supplements 1-5 published in Eur. J. Bio-chem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. http://enzyme.expasy.org/.

The term "mature polypeptide" means a polypeptide in its final form following translation and any post-translational modifications, such as N-terminal processing, C-terminal truncation, glycosylation, phosphorylation, etc. In an embodiment the mature polypeptide of the present disclosure is amino acids 19 to 281 of SEQ ID NO: 2 based on amino acid sequencing using Edman degradation chemistry. It is known in the art that a host cell may produce a mixture of two of more different mature polypeptides (i.e., with a different C-terminal and/or N-terminal amino acid) expressed by the same polynucleotide.

The term "nucleotide sequence encoding a mature polypeptide" as used herein means a polynucleotide that encodes a mature polypeptide of the present disclosure. In an embodiment the polynucleotide encoding a mature polypeptide is the sequence consisting of nucleotides 55 to 846 of SEQ ID NO: 1.

The term "very high stringency conditions" as used herein means for probes of at least 100 nucleotides in length, prehybridization and hybridization at 42° C. in 5×SSPE, 0.3% SOS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SOS at 70° C.

For "high stringency conditions" prehybridization and hybridization is carried out with 50% formamide and the carrier material is finally washed three times each for 15 minutes using 2×SSC, 0.2% SOS at 65° C.

For "medium-high stringency conditions" prehybridization and hybridization is carried out with 50% formamide and the carrier material is finally washed three times each for 15 minutes using 2×SSC, 0.2% SOS at 60° C.

For "medium stringency conditions" prehybridization and hybridization is carried out with 35% formamide and the carrier material is finally washed three times each for 15 minutes using 2×SSC, 0.2% SOS at 55° C.

For "low stringency conditions" prehybridization and hybridization is carried out with 25% formamide, and the carrier material is finally washed three times each for 15 minutes using 2×SSC, 0.2% SOS at 50° C.

For "very low stringency conditions" prehybridization and hybridization is carried out with 25% formamide and the carrier material is finally washed three times each for 15 minutes using 2×SSC, 0.2% SOS at 45° C.

The term "isolated" as used herein about a substance, means any substance, which by means of human intervention, has been put in a form or environment that differs from the form or environment in which it is found in nature. Isolated substances include but is no limited to polypeptides and/or polynucleotides for which the ratio of the polypeptide and/or polynucleotide relative to other constituents with which they are associated in nature is increased or decreased. In an important embodiment the amount of polypeptide and/or polynucleotide is increased relative to other constituents with the polypeptide and/or polynucleotide substance is associated in nature.

In an embodiment the polypeptides and/or polynucleotides may be isolated into a pure or substantially pure form. In this context a substantially pure polypeptide and/or polynucleotide means that the polypeptide and/or polynucleotide is separated from other extraneous or unwanted polypeptides and/or nucleotides. Such a substantially pure polypeptide and/or polynucleotide preparation contains less than 10%, such as less than 8%, such as less than 6%, such as less than 5%, such as less than 4%, such as less than 3%, such as less than 2%, such as less than 1%, such as less than 0.5% by weight of other distinct polypeptide and/or polynucleotide materials usually associated with the polypeptide and/or polynucleotide when expressed natively or recombinantly. In an embodiment the polypeptide and/or polynucleotide is at least 90% pure, such as at least 91% pure, such as at least 92% pure, such as at least 93% pure, such as at least 94% pure, such as at least 95% pure, such as at least 96% pure, such as at least 97% pure, such as at least 98% pure, such as at least 99% pure, such as at least 99.5% pure, such as 100% pure by weight. Purification of polypeptides can be accomplished, for example, by preparing the polypeptide by well-known recombinant methods or by classical purification methods.

The term "non-naturally occurring" as used herein about a substance, means any substance that is not normally found in nature or natural biological systems. In this context the term "found in nature or in natural biological systems" does not include the finding of a substance in nature resulting from releasing the substance to nature by deliberate or accidental human intervention. Non-naturally occurring substances may include substances completely or partially synthesized by human intervention and/or substances prepared by human modification of a natural substance.

The term "% identity" is used herein about the relatedness between two amino acid sequences or between two nucleotide sequences.

The term "% identity" as used herein about amino acid sequences means the degree of identity in percent between two amino acid sequences obtained when using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$\frac{\text{identical amino acid residues}}{\text{Length of alignment} - \text{total number of gaps in alignment}} \times 100$$

The term "% identity" as used herein about nucleotide sequences means the degree of identity in percent between two nucleotide sequences obtained when using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

$$\frac{\text{identical deoxyribonucleotides}}{\text{Length of alignment} - \text{total number of gaps in alignment}} \times 100$$

The protein sequences of the present invention can further be used as a "query sequence" to perform a search against sequence databases, for example to identify other family members or related sequences. Such searches can be performed using the BLAST programs. Software for performing BLAST analyses is publicly available through the National Center for Biotechnology Information (http://www.ncbi.nlm.nih.gov).

BLASTP is used for amino acid sequences and BLASTN for nucleotide sequences. The BLAST program uses as defaults:

Cost to open gap: default=5 for nucleotides/11 for proteins

Cost to extend gap: default=2 for nucleotides/1 for proteins

Penalty for nucleotide mismatch: default=–3

Reward for nucleotide match: default=1

Expect value: default=10

Wordsize: default=11 for nucleotides/28 for megablast/3 for proteins

Furthermore the degree of local identity between the amino acid sequence query or nucleic acid sequence query and the retrieved homologous sequences is determined by the BLAST program. However only those sequence segments are compared that give a match above a certain threshold. Accordingly the program calculates the identity only for these matching segments. Therefore the identity calculated in this way is referred to as local identity.

The term "functional polypeptide variant" as used herein means a polypeptide wherein one or more amino acids have been removed or deleted, changed or inserted in a parent mature polypeptide, while properties of parent mature polypeptide has been qualitatively preserved. In that context the term "qualitative" means that the type, but not necessarily the level, of a property of the parent mature polypeptide has been preserved. Also, in that context the term "changed" includes any alteration of amino acids in the parent mature polypeptide by substitution, mutation or chemical modification. In an embodiment a functional polypeptide variant may be a fragment of the parent mature polypeptide, where one or more amino acids has been removed from the amino and/or carboxyl terminus of the parent mature polypeptide. In another embodiment the functional polypeptide variant is an allelic polypeptide variant encoded by an allelic gene variant.

The term "allelic gene variant" as used herein means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a nucleotide sequence, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequence" as used herein means a nucleotide sequence necessary for expression of a polynucleotide encoding a polypeptide. A control sequence may be native (i.e., from the same gene) or foreign (i.e., from a different gene) to the polynucleotide encoding the polypeptide. Control sequences include, but are not limited to leader sequences, polyadenylation sequence, pro-peptide coding sequence, promoter sequences, signal peptide coding sequence, translation terminator (stop) sequences and transcription terminator (stop) sequences. To be operational control sequences usually must include promoter sequences, transcriptional and translational stop signals. Control sequences may be provided with linkers for the purpose of introducing specific restriction sites facilitating ligation of the control sequences with a coding region of a polynucleotide encoding a polypeptide.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression.

The term "functional polynucleotide variant" as used herein means a polynucleotide which encode a functional polypeptide variant.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "nucleic acid construct" means a nucleic acid molecule, either single- or double stranded, which is isolated from a naturally occurring gene or is modified to contain segments of nucleic acids in a manner that would not otherwise exist in nature or which is synthetic, and which comprises one or more control sequences.

The term "operably linked" means a configuration in which a control sequence is placed at an appropriate position relative to the coding polynucleotide such that the control sequence directs expression of the coding polynucleotide.

The term "complement" as used herein, refers to a nucleotide sequence which is sufficiently complementary to another nucleotide sequence so that the first nucleotide sequence hybridize to the other nucleotide sequence thereby forming a stable duplex. The first nucleotide sequence is thereby a complement to the second nucleotide sequence.

The terms "nucleotide sequence and "polynucleotide" are used herein interchangeably.

The term "comprise" and "include" as used throughout the specification and the accompanying claims as well as variations such as "comprises", "comprising", "includes" and "including" are to be interpreted inclusively. These words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The term "specificity" used herein refers to the property of an enzyme to catalyze a reaction turning a substrate into catalysis products. In one aspect an enzyme may display a) absolute specificity—meaning that the enzyme will catalyze a particular substrate reaction; b) group specificity—meaning that the enzyme will act on substrates that contain a specific functional group; c) linkage specificity—meaning that the enzyme will act on a particular type of chemical bond and/or d) stereo-chemical specificity—meaning that the enzyme will act on a particular steric or optical isomer.

The term "activity" used herein refers to the effectiveness of an enzyme in catalyzing the reaction turning a substrate for which the enzyme has specificity into catalysis products. Enzyme activity is usually calculated in Units, where a Unit is the amount of substrate hydrolyzed (in $\mu$mol) per weight of the enzyme (usually in gram) per time unit (usually minutes).

In particular polypeptides having lysozyme "specificity" refers to polypeptide enzymes belonging to EC 3.2.1.17 or to any of the CAZy glycoside hydrolase (GH) classes of GH22 (hen egg-white lysozyme), GH23 (goose egg-white lysozyme), GH24 (bacteriophage T4 lysozyme), GH73 (*Sphingomonas* flagellar protein) and GH25 (*Chalaropsis* lysozymes) and capable of catalyzing hydrolysis of glycosidic bonds in peptidoglycan or chitodextrin.

For purposes of the invention lysozyme may be determined by different assays. One assay described in (H. Maeda, J. Biochem., 1980, vol. 88 (4): 1185-1191) is based on either fluorescence polarization or fluorescence intensity using fluorescein-labeled cell wall peptidoglycan from *Micrococcus* lysodeikticus as a substrate.

Another assay, EnzChek® Lysozyme Assay Kit (E-22013), is available from Molecular Probes, and is also based on a measure of lysozyme activity on *Micrococcus* lysodeikticus cell walls that are labeled with fluorescein.

Another assay is based on the clearance of a *Micrococcus luteus* suspension caused by lysozyme and monitored at 450 nm and compared to a lysozyme standard of known activity. This assay was developed at the FIP Center for Standards, International Commission on Pharmaceutical Enzymes, Harelbekestaat 72, B-9000 gent, Belgium. This assay requires the use of lyophilized, viable *M. luteus* ATCC 4698 cells. This substrate is available from the Center for Standards as well as a detailed protocol.

For purposes of the present invention it is preferred to measure lysozyme activity by the assay described in Lysozyme activity assay described in the examples (infra).

The term "antimicrobial activity" used herein refers to the effectiveness of an antimicrobial agent, such as lysozyme in killing microorganisms or inhibiting their growth. In the case of bacteria antimicrobial activity therefore include both bactericidal activity (effectiveness in killing bacteria) bacteriostatic activity (effectiveness in inhibiting or prevent bacterial propagation/growth). For lysozyme antimicrobial effect may derive from this enzyme cell wall peptidoglycans or chitodextrin, it may derive from binding of lysozyme to the surface of a microorganism and inhibiting its growth, it may derive from lysozyme activating bacterial autolysins, from lysozyme acting as immunostimulator, from lysozyme acting by inhibiting or reducing bacterial toxins and/or by lysozyme causing opsonic effects.

For purposes of the present invention, antimicrobial activity is determined according to a suitable assay known in the art such as described in "Ultrasensitive assays for endogenous antimicrobial polypeptides; J. Immun. Met. Volume 137, Issue 2, 21 Mar. 1991, Pages 167-173"

Polypeptides

The polypeptides of the invention are lysozyme enzymes from the genus *Rasamsonia*, particularly lysozyme enzymes from *Rasamsonia emersonii*.

In an embodiment the lysozyme polypeptide comprises an amino acid sequence selected from the group consisting of
a) polypeptides having at least 70% identity to the mature polypeptide of SEQ ID NO:2
b) polypeptides encoded by a polynucleotide having at least 70% identity to the nucleotide sequence comprised in SEQ ID NO:1 encoding the mature polypeptide of SEQ ID NO:2 or genomic DNA thereof;
c) polypeptides encoded by a polynucleotide hybridizing under very low stringency conditions with the complement to the nucleotide sequence comprised in SEQ ID NO:1 encoding the mature polypeptide of SEQ ID NO:2 or genomic DNA thereof and
d) functional polypeptide variants of the mature polypeptide of (a), (b) or (c)

In a more specific embodiment the polypeptide of the present disclosure has at least 70%, such as at least 75%, such as at least 80%, such as at least 85%, a such as at least 90%, such as at least 91%, such as 91.8%, such as at least 92%, such as at least 93%, such as at least 94%, such as at least 95%, at least such as 96%, such as at least 97%, such as at least 98%, such as at least 99%, such as at least 99.25, such as at least 99.50, such as at least 99.75% identity to the mature polypeptide of SEQ ID NO:2. Even more specifically the polypeptide may comprise SEQ ID NO:2 or the mature polypeptide of SEQ ID NO:2, such as consist of amino acids 19 to 279 of SEQ ID NO:2. I a particular embodiment the polypeptide of the present disclosure has more than 91.7% identity, such as more than 92% identity, such as 93% identity to SEQ ID NO:2 or the mature polypeptide of SEQ ID NO:2 or amino acids 19 to 279 of SEQ ID NO:2.

In another embodiment the polypeptide of the present disclosure is encoded by a polynucleotide that has at least 70%, such as at least 75%, such as at least 80%, such as at least 85%, such as at least 90%, such as at least 91%, such as at least 92%, such as at least 93%, such as at least 94%, such as at least 95%, at least such as 96%, such as at least 97%, such as at least 98%, such as at least 99% identity to the nucleotide sequence comprised in SEQ ID NO:1 encoding the mature polypeptide of SEQ ID NO:2 or genomic DNA thereof. More specifically the polypeptide is encoded by a nucleotide comprising SEQ ID NO:1 or comprising the nucleotide sequence comprised in SEQ ID NO:1 encoding the mature polypeptide of SEQ ID NO:2 or genomic DNA thereof. Even more specifically, the polypeptide of the present disclosure is encoded by a polynucleotide consisting of the nucleotide sequence comprised in SEQ ID NO:1 encoding the mature polypeptide of SEQ ID NO:2 or genomic DNA thereof. Even more specifically, the polypeptide of the invention is encoded by a polynucleotide consisting of nucleotides 55 to 837 of SEQ ID NO:1 or genomic DNA thereof.

In another embodiment, the polypeptide of the present disclosure is encoded by a polynucleotide which hybridizes at stringency conditions selected from low stringency conditions, medium to low stringency conditions, medium stringency conditions, medium to high stringency conditions, high stringency conditions and very high stringency conditions with the complement to the nucleotide sequence comprised in SEQ ID NO:1 encoding the mature polypeptide of SEQ ID NO:2 or genomic DNA thereof. (Sambrook et al., 1989, Molecular Cloning, A Laboratory Manual, 2d edition, Cold Spring Harbor, N.Y.).

The nucleotide sequence of SEQ ID NO: 1 or a subsequence thereof, as well as the polypeptide of SEQ ID NO: 2 or a fragment thereof can be used to design nucleic acid probes suitable for identifying and cloning DNA, encoding polypeptides of the invention from strains of different genera or species according to methods well known in the art. Such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with 32P, 3H, 35S, biotin, or avidin). Such probes are encompassed by the present invention. A genomic DNA or cDNA library prepared from such other strains may be screened for DNA that hybridizes with the probes described above and encodes a polypeptide of the invention. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot. For purposes of the invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the complement thereof; or (iv) a subsequence thereof; under very low to very high stringency conditions. Molecules to which the nucleic acid probe hybridizes under these conditions can be detected using, for example, X-ray film or any other detection means known in the art.

In an embodiment the probe of nucleotides is SEQ ID NO:1 or is selected from nucleotides 55-837 of SEQ ID NO:1; from the sequence of SED ID NO:1 encoding the mature polypeptide of SEQ ID NO: 2 and from a fragment thereof.

In an important embodiment the sequence of the polypeptide of the invention is not a polypeptide from the strain deposited under CBS 394.64 or any sequence that has at least 95%, such as at least 96%, such as at least 97%, such as at least 98%, such as at least 99%, such as at least 99.5% identity to such polypeptide, which has lysozyme activity.

In a further embodiment the polypeptide of the invention is an allelic variant and/or a functional polypeptide variant of the mature polypeptide of the invention comprising a substitution, a deletion, and/or insertion at one or more amino acid positions. More specifically the allelic variant and/or the functional polypeptide variant of the invention comprise at least 2, such at least 3, such at least 4, such at least 5, such at least 6, such at least 7, such at least 8, such at least 9, such at least 10 substitutions, deletions, or insertions or a combination thereof. In another embodiment the number of substitutions, deletions, or insertions or a combination thereof is no more than 20, such as 19, 18, 17, 16, 15, 14, 13, 12, or 11.

The amino acid changes (substitution, deletion, and/or insertion) may be minor and conservative in that they do not significantly affect the folding and/or activity of the polypeptide. Conservative changes include small deletions, typically of 1-30 amino acids; small amino- or carboxyl-terminal extensions, such as an amino-terminal methionine residues; small linker peptides of up to 20-25 residues; small extensions which facilitate purification e.g. by altering the net charge, altering the poly-histidine tract, altering an antigenic epitope or altering a binding domain. Examples of conservative substitutions are substitutions among members of the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are well known e.g. from H. Neurath and R. L. Hill, 1979, The Proteins, Academic Press, New York. Common substitutions are Ala<->Ser, Val<->lie, Asp<->Glu, Thr<->Ser, Ala<->Gly, Ala<->Thr, Ser<->Asn, Ala<->Val, Ser<->Gly, Tyr<->Phe, Ala<->Pro, Lys<->Arg, Asp<->Asn, Leu<->Ile, Leu<->Val, Ala<->Glu, and Asp<->Gly. In a further embodiment the amino acid changes alter the physico-chemical properties of the polypeptides, such as the thermal stability, the substrate specificity, the pH optimum, the temperature optimum and other properties. Important amino acids in a polypeptide can be identified by known procedures such as site-directed mutagenesis or alanine-scanning mutagenesis (Cunningham and Wells, 1989, Science 244: 1081-1085 and/or Hilton et al., 1996, J. Biol. Chem. 271: 4699-4708). In alanine-scanning mutagenesis, single alanine mutations are introduced at every residue in the molecule, and the resulting altered molecules are tested for relevant activity for identifying amino acids critical for polypeptide activity. Important amino acids can also be identified by combining amino acid changes e.g. with nuclear magnetic resonance, crystallography, electron diffraction, or photo affinity labelling analysis revealing important physical structures of the polypeptide such as active site or other locations of biological interaction (de Vos et al., 1992, Science 255: 306-312; Smith et al., 1992, J. Mol. Biol. 224: 899-904 and Wlodaver et al., 1992, FEBS Lett. 309: 59-64). Single or multiple amino acid changes can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413 and WO 95/22625. Other methods that can be used include error-prone PCR, phage display (e.g., Lowman et al., 1991, Biochemistry 30: 10832-10837, U.S. Pat. No. 5,223,409 and WO 92/06204), and region-directed mutagenesis (Derbyshire et al., 1986, Gene 46: 145 and Ner et al., 1988, DNA, 7: 127). Mutagenesis/shuffling methods can be combined with high-throughput, automated screening methods to detect activity of cloned, mutagenized polypeptides expressed by host cells (Ness et al., 1999, Nature Biotechnology, 17: 893-896). Mutagenized DNA molecules that encode active polypeptides can be recovered from the host cells and rapidly sequenced using known standard methods. These methods allow the rapid determination of the importance of individual amino acid residues in a polypeptide.

In a further embodiment, the polypeptide of the invention, excluding any signal peptide, attached hybrid or glycosylation moieties or protective agent (see below), has a molecular weight of between 10 to 50 kilo Daltons, such as 20 to 40 kilo Daltons, such as 25 to 30 kilo Daltons, such as 27 to 28 kilo Daltons such as about 27.6 kilo Daltons.

In a further embodiment, the polypeptide of the invention including the signal peptide, but excluding any attached hybrid or glycosylation moieties or protective agent (see below), has a molecular weight of between 10 to 50 kilo Daltons, such as 20 to 40 kilo Daltons, such as 25 to 35 kilo Daltons, such as 29 to 30 kilo Daltons such as about 29.4 kilo Daltons.

It is contemplated that the molecular weight is an important property of lysozyme enzymes, since it influences the enzymes ability to overcome steric hindrances at the bacterial surface that lowers or even prevents the enzymes access to the target site for hydrolytic cleavage.

In further separate embodiments, the polypeptide of the present disclosure, excluding any signal peptide, attached hybrid or glycosylation moieties or protective agent (see below) has one or more of the properties selected from one or more of:

a) an acidic isoelectric point (pI) between 2 and 7, such as between 3 and 6, such as between 3.5 and 4.5, e.g. between 3.9 and 4.0;

b) an acidic pH optimum between 3 and 7, such as between 4 and 6, such as between 4.5 and 5.5, such as about 5;

c) a temperature optimum between 40 and 80 degrees Celsius, such as between 50 and 70 degrees celcius, such between 55 and 65 degrees Celsius, such as about 60 degrees Celsius.

In further separate embodiments, the polypeptide of the present disclosure including the signal peptide, but excluding any attached hybrid or glycosylation moieties or protective agent (see below) has one or more of the properties selected from one or more of:
a) an acidic isoelectric point (ph between 2 and 7, such as between 3 and 6, such as between 3.5 and 4.5, e.g. between 4.0 and 4.1.
b) an acidic pH optimum between 3 and 7, such as between 4 and 6, such as between 4.5 and 5.5, such as about 5;
c) a temperature optimum between 40 and 80 degrees celcius, such as between 50 and 70 degrees Celsius, such between 55 and 65 degrees Celsius, such as about 60 degrees Celsius.

Moreover, the polypeptide of the invention may be a naturally occurring polypeptide or a non-natural or recombinant polypeptide prepared by human intervention.

Still further, the polypeptide of the present disclosure may be in isolated form.

In a further embodiment, the polypeptide of the present disclosure is a hybrid and/or a glycosylated polypeptide, wherein the polypeptide of the invention is bound to one more additional moieties, either during or post transcription.

In the case of hybrid polypeptides, the hybrid polypeptide comprise one or more additional polypeptides covalently bound to the polypeptide of the invention. Here the polypeptide of the invention may be fused at the N-terminus and/or the C-terminus to the N-terminus and/or the C-terminus of the additional polypeptide. The additional polypeptide may provide additional properties such as substrate binding properties or solubility properties or increase in one or more enzyme activities. The polypeptide of the invention and the additional polypeptide may be fused via a linker moieties. The fusion polypeptide of the invention may further comprise a cleavage site between the two or more polypeptides, optionally in the linker moiety allowing the fused polypeptides to be separated at a later stage if so desired. Examples of cleavage sites include those disclosed in Martin et al., 2003, J. Ind. Microbial. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; Contreras et al., 1991, Biotechnology 9: 378-381; Eaton et al., 1986, Biochemistry 25: 505-512; Collins-Rade et al., 1995, Biotechnology 13: 982-987; Carter et al., 1989, Proteins: Structure, Function, and Genetics 6: 240-248; and Stevens, 2003, Drug Discovery World 4: 35-48. A hybrid polypeptide can be made by fusing a polynucleotide encoding the additional polypeptide and optionally a linker to polynucleotide of the invention. Well known techniques for producing such fused polypeptides include ligating sequences encoding the fused polypeptides, so that they are in frame and under control of the same promoter(s) and terminator. Fused polypeptides may also be constructed using "intein" technology in which fusion of polypeptides are achieved post-translationally (Cooper et al., 1993, EMBO J. 12: 2575-2583 and Dawson et al., 1994, Science 266: 776-779).

In the case of glycosylated polypeptides, the glycosylated polypeptide of the invention comprise a glycosyl moiety. The polypeptide of the invention may also be subjected to "hyperglycosylation" as described for example in Nakamura et al., *J Biol Chem.* 268(17):12706-12 (1993), incorporated herein by reference To improve the suitability of the polypeptide of the present disclosure for use with humans or animals, it may be advantageous to lower the immunogenicity and/or antigenicity of the polypeptide, thereby for example increasing its half-life if administered to a human or animal. Lowering of polypeptide antigenicity may be accomplished in a variety of ways, including masking immunogenic/antigenic surface residues and/or epitopes of the polypeptide from the immune system of a patient, by covalent and/or non-covalent coupling polymeric compounds to the surface of the polypeptide. One such polymeric compound is polyethylene glycol or PEG and coupling of PEG to polypeptides for reducing antigenicity is known as "PEGylation". In addition PEGylation may even improve other properties of the polypeptides such as activity, solubility, pH and temperature properties. The PEG can be linear chain or branched PEG's, and methods of PEGylation is known in the art. In a particular embodiment, the polypeptide of the invention is PEGylated with methoxypolyethylene glycol or succinimidyl succinate (MPSS) or a combination thereof.

In a further embodiment the additional moiety bound to the polypeptide of the invention is a polyethylene glycol (PEG) moiety. The PEG may be linear or branched or a combination thereof.

Still further, the polypeptide of the present disclosure may be attached to a polyethylene glycol in an amount sufficient to make the polypeptide less immunogenic and/or antigenic and/or to increase the half-life of the polypeptide in a human or animal.

Under certain conditions, PEGylation may however also interfere negatively with enzymatic activity for example if the attached PEG interferes with or blocks access to the active site of the enzyme or interferes with the catalytic reaction. To avoid this drawback, the active site can be protected by reversibly attaching a protective agent such as an inhibitor to the active site before PEGylation, to avoid attachment of PEG near or in the active site. After PEGylation this agent can then be removed again to restore the activity of the enzyme.

Accordingly, in a particular embodiment the polypeptide of the present disclosure comprises a protective agent reversibly attached to or near the active site of the polypeptide. In a further embodiment the protective agent is a chitosan oligosaccharide or a glucosamine monomer or a glucosamine polymer. Particularly the protective agent is a tetraglucosamine or a heptaglucosamine.

Signal/Propeptide

The present disclosure also provide a signal and/or propeptide comprising amino acids 1 to 8 of SEQ ID NO:2 or a variant thereof having at least 70% identity to amino acids 1 to 18 of SEQ ID NO:2. Moreover the present disclosure also provides a nucleotide sequence encoding the signal or propeptide comprising nucleotides 1 to 54 of SEQ ID NO:1, or a variant thereof having at least 70% identity to nucleotides 1 to 54 of SEQ ID NO:1

Polynucleotides

The present disclosure also provides polynucleotides encoding the polypeptides of the invention thereof. In a more specific embodiment the polynucleotide of the present disclosure comprises a nucleic acid sequence having at least 70%, such as at least 75%, such as at least 80%, such as at least 85%, such as at least 90%, such as at least 91%, such as at least 92%, such as at least 93%, such as at least 94%, such as at least 95%, at least such as 96%, such as at least 97%, such as at least 98%, such as at least 99% identity to the SEQ ID NO:1 or genomic DNA thereof. In a still further specific embodiment the polynucleotide of the invention comprises SEQ ID NO:1 or genomic DNA thereof or even more specifically comprises the nucleotide sequence comprised in SEQ ID NO:1 encoding the mature polypeptide of SEQ ID NO:2 or genomic DNA thereof. The polynucleotide of the invention may even consist of nucleotides 55 to 837 of SEQ ID NO: 1.

In a further embodiment the polynucleotide of the present disclosure may also be a polynucleotide which hybridizes under stringency conditions selected from low stringency conditions, medium to low stringency conditions, medium stringency conditions, medium to high stringency conditions, high stringency conditions or very high stringency conditions with the complement to the nucleotide sequence of SEQ ID NO:1 or genomic DNA thereof. More specifically and at these stringency conditions the polynucleotide of the invention hybridizes with the complement to the nucleotide sequence comprised in SEQ ID NO:1 encoding the mature polypeptide of SEQ ID NO:2 or genomic DNA thereof. Even more specifically the polynucleotide of the invention hybridizes with the complement to nucleotides 1-837 of SEQ ID NO:1 or even more specifically nucleotides 55-837 of SEQ ID NO:1 or genomic DNA thereof.

In a further embodiment the polynucleotide of the present disclosure is a functional polynucleotide variant or an allelic variant as defined herein. This variant may include nucleotide substitutions which that do not cause a change in the amino acid sequence of the encoded polypeptide, but which correspond to the codon usage of the host organism intended for production of the polypeptide, or may include nucleotide substitutions that which that do cause a different amino acid sequence. Techniques for nucleotide substitution are well known e.g. from Ford et al., 1991, Protein Expression and Purification 2: 95-107.

Still further, the polynucleotide of the invention may be in isolated form.

Moreover, the polynucleotide of the invention may be a naturally occurring polynucleotide or a non-natural or recombinant polynucleotide prepared by human intervention.

Techniques for preparing and/or isolating and/or cloning polynucleotides are well known and include classical methods of isolation of the polynucleotide from genomic DNA or cDNA, or a combination thereof or more modern methods of preparing synthetic polynucleotides. The cloning of polynucleotides from genomic DNA can accomplished e.g., by using the well-known polymerase chain reaction (PCR) or antibody screening of expression libraries to detect cloned DNA fragments with shared structural features (e.g., Innis et al., 1990, PCR: A Guide to Methods and Application, Academic Press, New York). Alternative nucleic acid amplification procedures include ligase chain reaction, ligation activated transcription and polynucleotide-based amplification. The polynucleotide may be cloned from a strain of *Rasamsonia emersonii* and may be an allelic or species variant of the polypeptide encoding region of the polynucleotide.

Nucleotide Constructs

The present disclosure also provides nucleic acid constructs comprising the polynucleotide of the invention and wherein the polynucleotide is operably linked to one or more control sequences, which direct the expression of a polypeptide from the polynucleotide in a microbial cell harbouring the nucleic acid construct. Conditions for the expression should be compatible with the control sequences.

A polynucleotide may be manipulated in a variety of ways allow expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, which is a polynucleotide that is recognized by a host cell for expression of a polynucleotide. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

The promoter may be an inducible promoter, such as a peptidoglycan or chitodextrin inducible promoter (i.e. a promoter inducible by peptidoglycan or chitodextrin present in bacterial cell walls). The promotor may also advantageously be inducible by other inducers depending on the conditions selected for the expression of the polypeptide of the invention. Such promotors may be selected from a) starch inducible promotors (including monomers, dimers and oligomers thereof, such as for example a maltose-inducible promoter or isomaltose-inducible promoter), b) cellulose-inducible promoters (i.e. a promoter inducible by cellulose, monomers, dimers and/or oligomers thereof, such as for example cellobiose-inducible promoters or sophorose-inducible promoters), c) hemicellulose inducible promoters (i.e. promoters inducible by hemicellulose, monomers, dimers, and/or oligomers thereof, such as xylan-inducible promoters, d) arabinose-inducible promoters or xylose-inducible promoters), e) pectin-inducible promoters (i.e. promoters inducible by pectin, monomers, dimers and/or oligomers thereof such as for example galacturonic acid-inducible promoters, f) rhamnose-inducible promoters), g) arabinan-inducible promoters (i.e. promoters inducible by arabinan, monomers, dimers, and/or oligomers thereof such as for example arabinose-inducible promoters), h) glucose-inducible promoter, i) lactose-inducible promoters and j) galactose-inducible promoters. Other inducible promoters are copper-, oleic acid-inducible promoters.

Examples of suitable promoters for directing transcription of the nucleic acid construct of the present disclosure in a filamentous fungal host cell are promoters obtained from the genes for *Aspergillus nidulans* acetamidase, *Aspergillus niger* neutral α-amylase, *Aspergillus niger* acid stable α-amylase. *Aspergillus niger* or *Aspergillus awamori* glucoamylase (glaA), *Aspergillus* gpdA promoter, *Aspergillus oryzae* TAKA amylase, *Aspergillus oryzae* alkaline protease, *Aspergillus oryzae* triose phosphate isomerase, *A. niger* or *A. awamori* endoxylanase (xlnA) or β-xylosidase (xlnD), *Fusarium oxysporum* trypsin-like protease (WO 96/00787), *Fusarium venenatum* amyloglucosidase (WO00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* β-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* β-xylosidase, as well as the NA2-tpi promoter and mutant, truncated, and hybrid promoters thereof. NA2-tpi promoter is a modified promoter from an

*Aspergillus* neutral α-amylase gene in which the untranslated leader has been replaced by an untranslated leader from an *Aspergillus* triose phosphate isomerase gene. Examples of such promoters include modified promoters from an *Aspergillus niger* neutral α-amylase gene in which the untranslated leader has been replaced by an untranslated leader from an *Aspergillus nidulans* or *Aspergillus oryzae* triose phosphate isomerase gene. Other examples of promoters are the promoters described in WO2006/092396, WO2005/100573 and WO2008/098933, incorporated herein by reference.

Examples of suitable promoters for directing transcription of the nucleic acid construct of the invention in a yeast host are promoters obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used.

Useful terminators for filamentous fungal host cells are obtained from the genes for
*Aspergillus nidulans* anthranilate synthase, *Aspergillus niger* glucoamylase, *Aspergillus niger* α-glucosidase, *Aspergillus oryzae* TAKA amylase, and *Fusarium oxysporum* trypsin-like protease.

Useful terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* α-factor, and *Saccharomyces cerevisiae* alcohol
dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Useful polyadenylation sequences for filamentous fungal host cells are obtained from the genes for *Aspergillus nidulans* anthranilate synthase, *Aspergillus niger* glucoamylase, *Aspergillus niger* α-glucosidase *Aspergillus oryzae* TAKA amylase, and *Fusarium oxysporum* trypsin-like protease.

Useful polyadenylation sequences for yeast host cells are described by Guo and Sherman, 1995, Mol. Cellular Biol. 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Useful signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* α-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide.

The propeptide coding sequence may be obtained from the genes for *Myceliophthora thermophila* laccase (WO 95/33836), *Rhizomucor miehei* aspartic proteinase, and *Saccharomyces cerevisiae* α-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound.

In filamentous fungi, the *Aspergillus niger* glucoamylase promoter, *Aspergillus oryzae* TAKA α-amylase promoter, and *Aspergillus oryzae* glucoamylase promoter may be used.

In yeast, the ADH2 system or GAL 1 system may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present disclosure also provides a recombinant expression vector comprising a polynucleotide of the invention, a promoter sequence and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression. The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid. The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may, when introduced into the host cell, integrate into the genome and replicate together with the chromosome(s) into which it has been integrated. Furthermore, a single vector or plasmid or two or more vectors or plasmids that together contain the total DNA to be introduced into the genome of the host cell, or a transposon, may be used. The vector preferably contains one or more selectable markers that permit easy selection of transformed, transfected, transduced, or the like cells. A selectable marker is a gene from which the product provides for biocide or viral resistance, resistance to heavy metals, prototrophy to auxotrophs, and the like.

Useful selectable markers for filamentous fungal host cell include amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. *Aspergillus nidulans* or *Aspergillus oryzae* amdS and pyrG genes and a *Streptomyces hygroscopicus* bar gene are particularly useful in *Aspergillus* cells.

Useful selectable markers for yeast host cells include, but are not limited to, ADE2, HIS3, LEU2, LYS2, MET3, TRP1, and URA3.

The vector preferably contains element(s) that permits integration of the vector into the host cell's genome or permits autonomous replication of the vector in the cell independent of the genome. For integration into the host cell genome, the vector may rely on the polynucleotide encoding the polypeptide or any other element of the vector for integration into the genome by homologous or non-homologous recombination. Alternatively, the vector may contain additional polynucleotides for directing integration by homologous recombination into the genome of the host cell at precise location(s) in the chromosome(s). To increase the likelihood of integration at a precise location, the integrational elements should contain a sufficient number of nucleic acids, such as 100 to 10,000 base pairs, such as 400 to 10,000 base pairs, and such as 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Useful origins of replication for filamentous fungal cell include AMA 1 and ANSI (Gems et al., 1991, Gene 98: 61-67; Cullen et al., 1987, Nucleic Acids Res. 15: 9163-9175; WO 00/24883). Isolation of the AMA 1 gene and construction of plasmids or vectors comprising the gene can be accomplished using the methods disclosed in WO 00/24883.

Useful origins of replication for yeast host cell are the 2 micron origin of replication, ARS1, ARS4, the combination of ARS1 and CEN3, and the combination of ARS4 and CEN6.

More than one copy of the polynucleotide of the invention may be inserted into a host cell to increase production of a polypeptide. An increase in the number of copies of the polynucleotide can be obtained by integrating at least one additional copy of the sequence into the host cell genome or by including an amplifiable selectable marker gene with the polynucleotide, so that cells containing amplified copies of the selectable marker gene—and thereby additional copies of the polynucleotide—can be selected by cultivating the cells in the presence of the appropriate selectable agent. The procedures used to ligate the elements described above to construct the recombinant expression vectors of the present invention are well known to one skilled in the art (see, e.g., Sambrook et al., 1989, supra).

Polypeptide Source

Polypeptides of the invention may be obtained from any suitable origin, including bacterial, fungal, yeast, plant, or mammalian origin. The term "obtained" also means herein that the enzyme may have been produced natively in an organism natively expressing the polypeptide or recombinantly in a host organism employing methods described herein, wherein the recombinantly produced enzyme is either native or foreign to the host organism or has a modified amino acid sequence comprising one or more amino acids deletions, insertions and/or substitutions compared to the native polypeptide. Strains of suitable source microorganisms are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), Agricultural Research Service Patent Culture Collection, Northern Regional Research Center (NRRL) and All-Russian Collection of Microorganisms of Russian Academy of Sciences, (abbreviation in Russian—VKM, abbreviation in English—RCM), Moscow, Russia. In an embodiment the source microorganism is a fungal strain, such as *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Rasamsonia, Thermoascus, Thielavia, Tolypocladium,* and *Trichoderma*. One suitable source microorganism is the strain of *Rasamsonia emersonii* publically available under the accession number NBRC 31070.

Polypeptides of the invention may also be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Host Cells

The present disclosure also provide a host cell, comprising a polynucleotide of the invention operably linked to one or more control sequences that direct the production of a polypeptide of the invention, e.g. in the form of the nucleotide construct or the vector as described herein (supra). The host cell is preferable recombinant. The construct or vector comprising the polynucleotide of the invention may be introduced into a host cell so that the construct or vector is maintained as a chromosomal integrant or as a self-replicating extra-chromosomal vector as described supra. The term "host cell" encompasses any progeny of a parent cell that is not identical to the parent cell due to mutations that occur during replication. The choice of a host cell will to a great extent depend upon the gene encoding the polypeptide and its source.

The host cell may be any cell useful in the recombinant production of a polypeptide of the present invention, particularly eukaryotes.

Strains of suitable host cell microorganisms are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), Agricultural Research Service Patent Culture Collection, Northern Regional Research Center (NRRL) and All-Russian Collection of Microorganisms of Russian Academy of Sciences, (abbreviation in Russian—VKM, abbreviation in English—RCM), Moscow, Russia.

In a particular embodiment, the host cell may is eukaryote, such as a mammalian, insect, plant, or fungal cell. The host cell is preferably a fungal cell. "Fungi" as used herein include the phyla Ascomycota, Basidiomycota, Chytridiomycota, and Zygomycota as well as the Oomycota and all mitosporic fungi as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacterial. Symposium Series No. 9, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth by hyphal elongation and carbon catabolism is obligately aerobic. In contrast, vegetative growth by yeasts such as *Saccharomyces cerevisiae* by budding of a unicellular thallus and carbon catabolism may be fermentative. The filamentous fungal host cell may be an *Acremonium, Aspergillus, Aureobasidium, Bjerkandera, Ceriporiopsis, Chrysosporium, Coprinus, Corio/us, Cryptococus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichodermacell*. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporiuminops, Chrysosporiumkeratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Corio/us hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichodermareesei,* or *Trichodermaviride* cell.

Useful fungal strains in the context of the present invention may be *Aspergillus niger* (CBS 513.88 and/or CBS 124.903), *Aspergillus oryzae* (ATCC 20423, IFO 4177, ATCC 1011, CBS205.89, ATCC 9576, ATCC14488-14491, ATCC 11601 and/or ATCC 12892), *P. chrysogenum* (CBS 455.95, ATCC 28089 and/or P2), *Penicillium citrinum* (ATCC 38065), *Thielavia terrestris* (NRRL8126), *Talaromyces emersonii* (CBS 124.902), *Acremonium chrysogenum* (ATCC 36225 and/or ATCC 48272), *Trichoderma reesei* (ATCC 26921, ATCC 56765 and/or ATCC 26921), *Aspergillus sojae* (ATCC 11906), *Myceliophthora thermophila*

(C1, Garg 27K and/or VKM-F 3500 D), *Chrysosporium lucknowense* (C1, Garg 27K, VKM-F 3500 D and/or ATCC 44006) and derivatives thereof.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacterial. 153: 163; and Hinnen et al., 1978, Proc. Natl. Acad. Sci. USA 75: 1920.

The host cell of the invention may also be altered by deleting, knocking-out or disrupting one or more genes in full or in part.

The host cell of the present disclosure may be formulated into a liquid or dry preparation. Dry formulations include lyophilizing, flash freezing or encapsulating the host cell.

Compositions

The present disclosure further provide compositions comprising the polypeptide and/or the host cell of the invention and one or more auxiliary additives. In an embodiment the composition of the invention comprise an increased amount of the polypeptide or host cell of the invention compared to the amount of polypeptide or host cell present in the broth from which the composition is derived.

In an embodiment the composition of the present disclosure comprise the polypeptide or host cell of the invention as the major enzymatic or cellular component, e.g. a monocomponent composition.

In another embodiment the composition of the present disclosure comprise one or more additional enzymes, in particular enzymes selected from cellulase, hemicellulase, cellobiohydrolase, pullulanase, glucanase, glucosidase, xylanase, xylosidase, mannanase, mannosidase, trehalase, glucoronidase, rhamnosidase, levanase, pectinase, lyase, amylase, cutinase, xanthanases, oxidoreductase, lipase, protease, AA9 (GH61) polypeptide, esterase, laccase, ligninase or lignin modifying enzyme, arabinase, arabinofuranosidase, galactosidase, esterase, glucuronidase and xyloglucanase.

More specifically the one or more additional enzymes may be selected from: lignin peroxidase, laccase, haloperoxygenase, catalase, pectin lyase, endo-β-1,4-glucanase, β-glucosidase, β-(1,3)(1,4)-glucanase, endoxylanase, β-xylosidase, α-L-arabinofuranosidase, α-D-glucuronidase, cellobiohydrolase, feruloyl esterase, coumaroyl esterase, α-galactosidase, β-galactosidase, β-mannanase, β-mannosidase, AA9(GH61), cellobiohydrolase I, cellobiohydrolase II, endoxylanase, α-L-arabinanase, acetyl mannan esterase, acetyl xylan esterase, glucuronoyl esterase, family 10 xylanase, manganese peroxidase, β-xylosidase, endo-polygalacturonase, pectin methyl esterase, endo-galactanase, pectin acetyl esterase, an endo-pectin lyase, pectate lyase, α rhamnosidase, exo-galacturonase, exo-polygalacturonate lyase, rhamnogalacturonan hydrolase, rhamnogalacturonan lyase, rhamnogalacturonan acetyl esterase, rhamnogalacturonan galacturonohydrolase, hexosyltransferase and xylogalacturonase.

The polypeptide or host cell compositions of the present disclosure may be prepared in accordance with methods known in the art into a liquid or a dry formulation including crude fermentation broths with or without cells removed, cell lysates with or without cellular debris, a semi-purified or purified polypeptide or host cell preparation.

Further, the composition may be in dry form such as a spray dried, spray cooled, lyophilized, flash frozen, granular, microgranular, capsule or microcapsule form made using methods known in the art.

Further, the composition may be in liquid form such as a stabilized liquid comprising one or more stabilizers such as sugars and/or polyols (e.g. sugar alcohols) and/or organic acids (e.g. lactic acid).

One or more of the additional enzymes of the composition may be wild-type proteins, recombinant proteins, or a combination of wild-type proteins and recombinant proteins.

Polypeptides comprised in the composition of the invention may include for example enzymes, from (1) commercial suppliers; (2) cloned genes expressing polypeptides, for example enzymes; (3) complex broth (such as that resulting from growth of a microbial strain in media, wherein the strains secrete proteins and enzymes into the media; (4) cell lysates of strains grown as in (3); and/or (5) plant material expressing polypeptides, for example enzymes. Different polypeptides in the composition of the invention may be obtained from different sources.

The composition of the present disclosure may also comprise other antimicrobial agents such as disinfectants, antiseptics or antibiotics. In a particular embodiment the composition of the invention comprise bactericidal agents such as beta-lactams (such as penicillin derivatives (penams), cephalosporins (cephems), monobactams, and carbapenems), vancomycin, daptomycin, fluoroquinolones, metronidazole, nitrofurantoin, co-trimoxazole or telithromycin.

In another embodiment the composition of the present disclosure comprise bacteriostatic agents such as bacteriostatic agents such as tetracyclines, Sulfonamides, Spectinomycin, Trimethoprim, Chloramphenicol, Macrolides, Lincosamides, Clindamycin, Ethambutol, Nitrofurantoin, Novobiocin, Tigecycline, Oxazolidinone, Erythromycin, Gentamycin, Meclocycline or sulfacetamide.

The composition of the present disclosure may also comprise any combination of the above mentioned additional compounds.

In further separate embodiments the composition of the present disclosure is:

a) a detergent composition comprising the polypeptide of the present disclosure and a surfactant;

b) A food composition comprising the polypeptide of the present disclosure and a nutrient suitable for human consumption;

c) A feed composition comprising the polypeptide of the present disclosure and a nutrient suitable for animal consumption;

d) A dentifrice composition comprising the polypeptide of the present disclosure and a cleansing agent suitable for oral use in a mammal and/or e) A cosmetic composition comprising the polypeptide of the present disclosure and a cleansing agent suitable for topical use on a mammal.

In a further embodiment the composition of the present disclosure is a pharmaceutical composition comprising the polypeptide of the invention and a pharmaceutically acceptable vehicle, carrier or excipient. Any suitable pharmaceutical vehicle, excipient or carrier that would commonly be used in this art could be chosen including saline, dextrose, water, glycerol, ethanol, other therapeutic compounds, and combinations thereof. As one skilled in this art would recognize, the particular vehicle, excipient or carrier used will vary depending on the patient and the patient's condition, and a variety of modes of administration would be suitable for the compositions of the invention, as would be recognized by one of ordinary skill in this art.

Methods of Manufacture

The present disclosure also provides a method for manufacturing a polypeptide of the invention, comprising cultivating a host cell of the invention under conditions allowing the cell to express the polypeptide and, optionally, recovering the expressed polypeptide. In one embodiment the host cell is a wild type cell, while in another embodiment the host cell is recombinant. In a further embodiment the cell is a strain of *Talaromyces, Rasamsonia, Aspergillus, Trichoderma* or *Pichia*.

The invention also provides a method for manufacturing a host cell of the invention comprising selecting one or more host cells of the invention and propagating them under conditions suitable for the cells to multiply and, optionally, isolating the cells.

The host cells are cultivated in a nutrient medium suitable for production of the polypeptide and/or propagating cell count using methods known in the art. For example, the host cells may be cultivated by shake flask cultivation, or small-scale or large-scale fermentation (including continuous, batch, fed-batch, or solid state fermentations) in laboratory or industrial fermenters in a suitable medium and under conditions allowing the polypeptide to be expressed and/or the host cells to propagate and optionally to be isolated.

The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The selection of the appropriate medium may be based on the choice of host cell and/or based on the regulatory requirements for the host cell. Such media are known to those skilled in the art. The medium may, if desired, contain additional components favoring the transformed expression hosts over other potentially contaminating microorganisms. Accordingly, in an embodiment a suitable nutrient medium comprise a carbon source (e.g. glucose, maltose, molasses, starch, cellulose, xylan, pectin, lignocellulolytic biomass hydrolysate, etc.), a nitrogen source (e. g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.). Optionally, additional inducers may be included (see above).

The cultivating of the host cell may be performed over a period of from about 0.5 to about 30 days. The cultivation process may be a batch process, continuous or fed-batch process, suitably performed at a temperature in the range of 0-100° C. or 0-80° C., for example, from about 0° C. to about 50° C. and/or at a pH, for example, from about 2 to about 10. Preferred fermentation conditions for *Pichia* or *Aspergillus* as host are a temperature in the range of from about 25° C. to about 35° C. and at a pH of from about 3 to about 9. Preferred fermentation conditions for *Trichoderma* as host are a temperature in the range of from about 40° C. to about 45° C. and at a pH of from about 3 to about 9. Preferred fermentation conditions for *Talaromyces* as host are a temperature in the range of from about 50° C. to about 55° C. and at a pH of from about 3 to about 9. The appropriate conditions are usually selected based on the choice of host cell and the polypeptide to be expressed.

If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide and/or host cells may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present disclosure expressing the polypeptide is used as a source of the polypeptide.

The present disclosure also provides an isolated plant, e.g., a transgenic plant, plant part, or plant cell, comprising a polynucleotide of the invention, the polynucleotide of the invention and/or the nucleic acid construct and/or vector of the invention and expressing and producing the polypeptide of the invention in useful quantities. The polypeptide may be recovered from the plant or plant part.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn). Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats. Also included within the scope of the present invention are the progeny of such plants, plant parts, and plant cells. The transgenic plant or plant cell expressing the polypeptide or domain may be constructed in accordance with methods known in the art. In short, the plant or plant cell is constructed by incorporating one or more expression constructs encoding the polypeptide of the invention into the plant host genome or chloroplast genome and propagating the resulting modified plant or plant cell into a transgenic plant or plant cell. The expression construct is conveniently a nucleic acid construct that comprises a polynucleotide encoding the polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used). The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, Plant Physiology 86: 506. For constitutive expression, the 358-CaMV, the maize ubiquitin 1, or the rice actin 1 promoter may be used (Franck et al., 1980, Cell 21: 285-294; Christensen et al., 1992, Plant Mol. Biol. 18: 675-689; Zhang et al., 1991, Plant Cell 3: 1155-1165). Organ-specific promoters may be, for example, a promoter from storage sink tissues such as seeds, potato tubers, and fruits (Edwards and Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant Cell Physiol. 39: 885-889), a *Vicia faba* promoter from the legumin B4 and the unknown seed protein gene from *Vicia faba* (Conrad et al., 1998, J. Plant Physiol. 152: 708-711), a promoter from a seed oil body protein (Chen et al., 1998, Plant Cell Physiol. 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiol. 102: 991-1000), the *chlorella* virus adenine methyltransferase gene promoter (Mitra and Higgins, 1994, Plant Mol. Biol. 26: 85-93), the aldP gene promoter from rice (Kagaya et al., 1995, Mol. Gen. Genet. 248: 668-674), or a wound inducible promoter such as the potato pin2 promoter (Xu et al., 1993, Plant Mol. Biol. 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals. A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression. The selectable marker gene and any other parts of the expression construct may be chosen from those available in the art. The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274). *Agrobacterium tumefaciens*-mediated gene transfer is a method for generating transgenic dicots (for a review, see Hooykas and Schilperoort, 1992, Plant Mol. Biol. 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, Plant J. 2: 275-281; Shimamoto, 1994, Curr. Opin. Biotechnol. 5: 158-162; Vasil et al., 1992, Bio/Technology 10: 667-674). An alternative method for transformation of monocots is based on protoplast transformation as described by Omirulleh et al., 1993, Plant Mol. Biol. 21: 415-428. Additional transformation methods include those described in U.S. Pat. Nos. 6,395,966 and 7,151,204 (both incorporated herein by reference in their entirety). Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase. In addition to direct transformation of a particular plant genotype with a construct of the invention, transgenic plants may be made by crossing a plant comprising the construct to a second plant lacking the construct. For example, a construct encoding a polypeptide can be introduced into a particular plant variety by crossing, without the need for ever directly transforming a plant of that given variety. Therefore, the invention encompasses not only a plant directly regenerated from cells which have been transformed in accordance with the invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204. Plants may be generated through a process of backcross conversion. For example, plants include plants referred to as a backcross converted genotype, line, inbred, or hybrid. Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized. The invention also provides methods of producing a polypeptide of the invention comprising cultivating a transgenic plant or a plant cell comprising a polynucleotide encoding the polypeptide or domain under conditions conducive for production of the polypeptide and optionally recovering the polypeptide.

Finally, as mentioned above, in the context of manufacture, the invention provides a method for reducing immunogenicity of a polypeptide of the invention comprising binding one or more PEG moieties to the polypeptide.

Methods of Using the Polypeptide

The invention further provides non-therapeutic use of the polypeptide of the invention for treating peptidoglycan or chitodextrin substrate. In particular the invention provides a method for treating a peptidoglycan or chitodextrin substrate comprising contacting said substrate with a polypeptide of the invention.

The term "treatment" as used in this context includes degradation and/or hydrolysis and/or modification of the substrates for the lysozyme. Degradation in this context implies that the treatment results in the generation of hydrolysis products of the substrates into subcomponents of the substrate which are smaller or shorter in length than the untreated substrate.

The substrates may be subjected to the polypeptide of the invention and any auxiliary additives such as additional enzymes in any suitable manner and combination.

In an embodiment the polypeptide of the invention is brought in contact with the substrate by producing the polypeptide exogenously in a yeast, fungi, algae or plant, isolating the polypeptide and adding it to the substrate. In another embodiment the polypeptide is brought in contact with the substrate by producing the polypeptide exogenously in a yeast, fungi, bacteria, algae or plant and adding more or less crude cell mass from the expression to the substrate. In a further embodiment, the crude cell mass or polypeptide production medium/material is treated to prevent further microbial growth (for example, by heating or addition of antimicrobial agents) and then added to the substrate. The polypeptide, crude cell mass and/or any auxiliary additives can be used concomitantly or sequentially or a combination thereof.

The substrate may be comprised in any composition or matrix in any suitable form.

The polypeptide of the present disclosure may be contacted and incubated with the substrates under any appropriate conditions. For example, the incubation can be performed at a temperature ranging from 25° C. to 95° C., such as from 30° C. to 90° C., such as from 35° C. to 85° C., such as from 37° C. to 80° C., such as from 37° C. to 75° C., such as from 37° C. to 70° C., such as from 37° C. to 65° C., such as from 37° C. to 60° C., such as from 37° C. to 55° C., such as from 37° C. to 50° C., such as from 37° C. to 45° C., such as from 37° C. to 40° C.

In combination with these temperature conditions the incubation may be performed at a pH ranging from pH 2.0 to pH 10, such as from pH 3.0 to pH 9, such as from pH 4.0 to pH 8.5, such as from pH 5 to pH 8, such as from pH 6.0 to pH 7.5, such as from pH 6.5 to pH 7.5.

Use of the polypeptide of the present disclosure includes killing and/or inhibiting of bacteria wherever such activity is sought and many application can be conceived such as in food or feed processing, for farm and livestock sanitation, for household sanitation, for hospital medical equipment sanitation, in fermentations and cleaning of fermentation equipment, in antimicrobial pharmaceuticals and for diagnostics. In particular the invention provides a method for killing or inhibiting a microorganism comprising contacting said substrate with a polypeptide of the invention. This use and method involves applying an effective amount of the polypeptide of the invention to a desired locus for killing and/or inhibiting bacteria. By effective amount is meant the amount necessary to kill and/or inhibit a desired amount of bacteria, and one skilled in the art would recognize that such an amount may differ depending on the nature and condition of the particular application and depending on the bacterium with sought to be killed and/or inhibited.

Protoblast Preparation

The polypeptide of the present disclosure may be used to remove cell walls of bacterial cells to produce protoplasts, which is the "naked" cell without its cell wall, such as described in Protoplast Formation and Regeneration in *Acetobacter Pasteurianus; Am. J. Bioeng. Biotech.*; (2013) Vol. 1 No. 2 pp. 37-43

Biofilm

The polypeptide of the invention may also be used or removing and/or inhibiting biofilm or killing and/or inhibiting a microorganism forming biofilm.

Food/Feed

Application of lysozyme for killing and/or inhibiting bacteria in food is known for example in cheese production (see eg. WO 05/080559). Lysozyme has also been used for food preservation (see eg. Hughey and Johnson (1987) Appl Environ Microbial 53:2165). As a food preservative, Lysozyme is a natural, organic alternative to many potential carcinogens.

In an embodiment the invention provides use of the polypeptide of the invention for killing and/or inhibiting a microorganism in a food composition. This use involves performing a method for killing and/or inhibiting a microorganism in a food composition comprising contacting the food composition with an effective amount of the polypeptide of the invention. In particular the food composition comprise material of animal origin such as meat.

In a particular embodiment the polypeptide of the present disclosure is used to kill or inhibit bacteria, such as *Listeria monocytogenes* and/or *Lactobacillus plantarum*, in milk.

In another particular embodiment the polypeptide of the present disclosure is used to kill or inhibit bacteria, such as *Clostridium tyrobutyricum, Bacillus cereus* and/or *Listeria monocytogenes* in cheeses, such as hard cheese or camembert cheese.

In another particular embodiment the polypeptide of the present disclosure is used to kill or inhibit bacteria, such as *Carnobacterium, Brochotrix thermosphacta, Pseudomonas fluorescens, Leuconostoc mesenteroides, Listeria monocytogenes* and/or lactic acid bacteria in meat and/or fish and/or products thereof, optionally using the polypeptide in combination with other active ingredients such as EDTA and/or Nisin In another particular embodiment the polypeptide of the present disclosure is used to kill or inhibit bacteria, such as *Oenococcus oeni, Lactobacillus* spp., *Pediococcus damnosus, Pediococcus parvulus, Lactobacillus brevis, Pediococcus damnosus* and/or *Shigella Typhimurium* in beverages such as wines, beers and/or fruit juices.

In another embodiment the present disclosure provides use of the polypeptide of the invention for killing and/or inhibiting a microorganism in a food processing facility. In this context the term "food processing facility" includes any facility designed for processing food for human beings and any objects included therein. This use involves performing a method for killing and/or inhibiting a microorganism in a food processing facility comprising contacting a food processing equipment with an effective amount of the polypeptide of the invention. In particular the food processing facility is a meat processing facility such as a slaughter house, a milk processing facility, such as a dairy or food cooking facility such as a restaurant.

In a particular embodiment the food processing facility also include packaging material and polypeptide of the present disclosure may be applied to packaging materials such as cellulose based materials and used to kill or inhibit bacteria in foods packed in such material, such as described in: *Antimicrobial activity of lysozyme and lactoferrin incorporated in cellulose-based food packaging; Food Control Volume* 26*, Issue* 2, August 2012, Pages 387-392.

The polypeptide is similarly useful for killing and/or inhibiting bacteria in animal feed (see for example WO 00/21381 and WO 04/026334), and in another embodiment the invention provides use of the polypeptide of the invention for killing and/or inhibiting a microorganism in an animal feed compositions. In this context the term "animal feed compositions" includes any type of pet food compositions. This use involves performing a method for killing and/or inhibiting a microorganism in an animal feed composition comprising contacting the animal feed composition with an effective amount of the polypeptide of the invention. In particular the animal feed composition comprise material of animal origin, in particular meat. Use of lysozyme can partially of fully replace other antibiotics in animal feed for improving (growth) performance in pigs, poultry, ruminants and/or farmed fish, shellfish or crustaceans.

In pig feed compositions effective dosing of Lysozyme is 30-600 mg per kg feed, preferably 100-300 mg/kg.

In another embodiment the present disclosure provides use of the polypeptide of the invention for killing and/or inhibiting a microorganism in an animal feed processing facility. In this context the term "animal feed" compositions includes any type of pet food and the term "animal feed processing facility" includes any facility designed for processing animal feed and any objects included therein. This use involves performing a method for killing and/or inhibiting a microorganism in an animal feed processing facility comprising contacting an animal feed processing equipment with an effective amount of the polypeptide of the invention.

Livestock Sanitation

In another embodiment the present disclosure provides use of the polypeptide of the invention for killing and/or inhibiting a microorganism in an agricultural facility. In this context the term "agricultural facility" includes any facility designed for housing any type of livestock or pets, including cow, pigs, chickens, turkeys, sheet, goats, cats, dog, horses and the like and any objects included therein. This use involves performing a method for killing and/or inhibiting a microorganism in an agricultural facility comprising contacting equipment used in an agricultural facility with an effective amount of the polypeptide of the invention.

Household Sanitation

In another embodiment the present disclosure provides use of the polypeptide of the invention for killing and/or inhibiting a microorganism in a household facility. In this context the term "household facility" includes any facility designed for accommodating human beings and any objects included therein, such as laundry, dishes and any hard surface object in a household facility that requires sanitation, such as floors, handles, bathrooms, toilets and the like. This use involves performing a method for killing and/or inhibiting a microorganism in a household facility comprising contacting the household facility with an effective amount of the polypeptide of the invention. In particular the polypeptide of the invention is used for killing and/or inhibiting a microorganism in laundry or dishes.

Hospital Sanitation

In another embodiment the present disclosure provides use of the polypeptide of the invention for killing and/or inhibiting a microorganism in a hospital facility. In this context the term "hospital facility" includes any facility designed for maintaining or restoring health of humans or animals and any objects included therein, such as clinical or surgical equipment, medical devices, implants and the like. This use involves performing a method for killing and/or inhibiting a microorganism in a hospital facility comprising contacting the hospital facility with an effective amount of the polypeptide of the invention.

Fermentations and CIP

In another embodiment the present disclosure provides use of the polypeptide of the present disclosure for killing and/or inhibiting a microorganism in a fermentation facility. In this context the term "fermentation facility" includes any facility designed for fermenting a microorganism any objects included therein, such as tanks, pipes, pumps, agitators, aerators, heaters, exchangers, filters and the like. This use involves performing a method for killing and/or inhibiting a microorganism in a fermentation facility comprising contacting the fermentation facility with an effective amount of the polypeptide of the present disclosure.

Health/Drugs

The present disclosure further provides therapeutic use of the polypeptide of the invention for treating peptidoglycan or chitodextrin substrate. Particularly, the invention provides a polypeptide or a host cell or a composition of the invention for killing and/or inhibiting a microorganism on or in a human or animal subject. More particularly the invention provides a polypeptide or a host cell or a composition of the invention for treating and/or preventing an infectious disease on or in a human or animal subject. Even more particularly the invention provides use of the polypeptide or the host cell or the composition of the invention for the preparation of a medicament for killing and/or inhibiting a microorganism on or in a human or animal subject. Even more particularly, the invention provides use of the polypeptide or the host cell or the composition of the invention for the preparation of a medicament for treating and/or preventing an infectious disease on or in a human or animal subject.

In further embodiments, the present disclosure provides a method for killing and/or inhibiting a microorganism on or in a human or animal subject, comprising administering an effective amount of the polypeptide or the host cell or the composition of the invention to the subject. In still further embodiments, the invention provides a method for treating or preventing an infectious disease on or in a human or animal subject comprising administering an effective amount of the polypeptide or the host cell or the composition of the invention to the subject.

The therapeutic or non-therapeutic use of the polypeptide, the host cell or the compositions of the invention may be directed towards oral care as disclosed in for example U.S. Pat. No. 4,355,022, WO 04/017988 or WO 08/124 764), towards cosmetology, dermatology, contraception, urology, and/or gynecology (see for example WO 08/124764).

With respect to human health the polypeptide may suitably be used for treating, inhibiting and/or preventing sexually transmitted diseases, tuberculosis, penicillin resistant infections such as MRSA and the like With respect to animal health the polypeptide may suitably be used for treating, inhibiting and/or preventing infectious diseases such as penicillin resistant infections such as MRSA and the like Particularly in pigs the polypeptide may suitably be used for treating, inhibiting and/or preventing conditions selected from sow syndrome, breast inflammation, uterine lesions, diarrhea as well as reduce or eliminate side effects, such as ugly fur, decreased feed intake, slow growth, by replacing alternative ingredients such as zinc oxide.

Particularly in meat poultry the polypeptide may suitably be used to improve resistance to diseases; to improve the intestinal canal; to promote growth and/or to increase the survival rate.

Particularly in egg poultry the polypeptide may suitably be used to repair the ovaries, to improve eggshell color, to increase laying rate, to extend the laying peak, to prevent bacterial infection when laying and/or to reduce mortality.

Particularly in ruminants the polypeptide may suitably be used for treating, inhibiting and/or preventing conditions selected from mastitis in dairy cows, and to improve milk yield during; to reducing somatic cell count in raw milk and/or to improve the quality of raw milk.

Particularly in farmed fish, shellfish or crustaceans the polypeptide may suitably be used for treating, inhibiting and/or preventing conditions selected from enteritis and/or inflammation and to improve growth, to reducing outer body damage and/or to improve the animals immune system and health status.

Suitable methods of administration of any polypeptide, hos cell or composition of the invention include, but are not limited to, topical, oral, anal, vaginal, intravenous, intraperitoneal, intramuscular, subcutaneous, intranasal and intradermal administration. In the desired composition, the composition will contain an effective amount of the lysozyme as described above so as to be useful in the methods as set forth herein. The compositions may additionally contain stabilizers or pharmaceutically acceptable preservatives, such as thimerosal (ethyl (2-mercaptobenzoate-S) mercury sodium salt) (Sigma Chemical Company, St. Louis, Mo.).

With regard to a human or animal subject, the effective amount would be that non-toxic amount of the lysozyme which would be administered to kill bacteria, the amount depending on the nature and condition of bacterium and the subject.

Kits and Antibodies

Still further, the invention also provides antibodies against the polypeptide of the present disclosure. These antibodies may target one or more epitopes of the polypeptide of the invention. Monoclonal antibodies of the invention may be produced using conventional means, e.g., the method of Kohler and Milstein, Nature 256:495-497 (1975), and polyclonal antibodies may be produced conventionally as well, e.g., by injection of an immunogenic amount of the protein of the invention into a suitable animal host, allowing sufficient time for the development of antibodies, and then recovering, isolating and/or purifying the antibodies obtained from the animal host. By immunogenic amount is meant that amount of the polypeptide of the invention which will provide an immunogenic reaction in the host so that the host generates antibodies to the injected protein. Accordingly, the invention provides an antibody capable of binding to one or more epitopes of the polypeptide of the invention. In this context an epitope is a part of the polypeptide that acts as an antigen which can be recognized by the immune system of a human or animal, specifically by antibodies, B cells, or T cells. The epitope may be conformational epitopes (discontinuous amino acid sequence) and/or linear (continuous amino acid sequence). In a particular embodiment the antibody is isolated and/or purified according to known methods and binds to a polypeptide of the invention having SEQ ID NO:2 as set forth above. These antibodies may take the form of monoclonal or polyclonal antibodies, and these antibodies can be useful in situations wherein it is desired to bind the polypeptide of the invention.

The antibody of the present disclosure can be used for detecting presence of the polypeptide of the invention. Accordingly, the invention provides a method of detecting the presence of a polypeptide comprising providing a sample suspected of containing the polypeptide, e.g., a blood or tissue sample of a subject, contacting the sample with an antibody of the invention, and detecting if binding between the antibody and a polypeptide in the sample has occurred.

Such diagnostic assays can be formed into a kit for detection of the polypeptide of the present disclosure and accordingly, the invention also provides a kit for detecting the polypeptide of the invention comprising a sample container, means for introducing the antibody to the sample, and means for detecting the binding of the antibody to the polypeptide in the sample. Such kits may utilize conventional labels or other means to detect binding.

Similarly, a kit of the present disclosure may also be constructed to detect the antibody of the invention, and the invention also provides a kit for detecting the antibody of the invention comprising a sample container, means for introducing the polypeptide to the sample, and means for detecting the binding of the polypeptide to the antibody in the sample. Such detection means may include suitable labels and will also allow for the quantification of the antibody titer in the sample.

Items of the Invention

1. A lysozyme enzyme from *Rasamsonia*.
2. A lysozyme enzyme from *Rasamsonia emersonii*.
3. A polypeptide of items 1-3 comprising an amino acid sequence selected from the group consisting of
a) a polypeptide having at least 70% identity to the mature polypeptide of SEQ ID NO:2
b) a polypeptide encoded by a polynucleotide having at least 70% identity to the nucleotide sequence comprised in SEQ ID NO:1 encoding the mature polypeptide of SEQ ID NO:2 or genomic DNA thereof;
c) a polypeptide encoded by a polynucleotide hybridizing under very low stringency conditions with the complement to the nucleotide sequence comprised in SEQ ID NO:1 encoding the mature polypeptide of SEQ ID NO:2 or genomic DNA thereof and
d) a functional polypeptide variant of the mature polypeptide of (a), (b) or (c)
4. The polypeptide of item 3, wherein the polypeptide of a) has at least 75%, such as at least 80%, such as at least 85%, a such as at least 90%, such as at least 91%, such as at least 92%, such as at least 93%, such as at least 94%, such as at least 95%, at least such as 96%, such as at least 97%, such as at least 98%, such as at least 99%, such as at least 99.25, such as at least 99.50, such as at least 99.75% identity to the mature polypeptide of SEQ ID NO:2.
5. The polypeptide of item 3, comprising SEQ ID NO:2 or the mature polypeptide of SEQ ID NO:2.
6. The polypeptide of item 3, consisting of amino acids 19 to 279 of SEQ ID NO:2.
7. The polypeptide of item 3, wherein the polynucleotide of b) encoding the polypeptide has at least 70%, such as at least 80%, such as at least 85%, a such as at least 90%, such as at least 91%, such as at least 92%, such as at least 93%, such as at least 94%, such as at least 95%, at least such as 96%, such as at least 97%, such as at least 98%, such as at least 99%, such as at least 99.25, such as at least 99.50, such as at least 99.75% identity to the nucleotide sequence comprised in SEQ ID NO:1 encoding the mature polypeptide of SEQ ID NO:2 or genomic DNA thereof.
8. The polypeptide of item 7, wherein the polynucleotide of b) encoding the polypeptide comprise SEQ ID NO:1 or the nucleotide sequence comprised in SEQ ID NO:1 encoding the mature polypeptide of SEQ ID NO:2 or genomic DNA thereof.

9. The polypeptide of item 8, wherein the polynucleotide of b) encoding the polypeptide consists of the nucleotide sequence comprised in SEQ ID NO:1 encoding the mature polypeptide of SEQ ID NO:2 or genomic DNA thereof.

10. The polypeptide of item 9, wherein the polynucleotide of b) encoding the polypeptide consists of nucleotides 55-837 of SEQ ID NO:1 or genomic DNA thereof.

11. The polypeptide of item 3, wherein the polynucleotide of c) hybridizes at stringency conditions selected from low stringency conditions, medium to low stringency conditions, medium stringency conditions, medium to high stringency conditions, high stringency conditions and very high stringency conditions with the complement to the nucleotide sequence comprised in SEQ ID NO:1 encoding the mature polypeptide of SEQ ID NO:2 or genomic DNA thereof.

12. The polypeptide of item 3, wherein the functional polypeptide variant of the mature polypeptide of c) comprises a substitution, a deletion, and/or insertion at one or more amino acid positions.

13. The polypeptide of item 12, comprising at least 2, such at least 3, such at least 4, such at least 5, such at least 6, such at least 7, such at least 8, such at least 9, such at least 10 substitutions, deletions, or insertions or a combination thereof. 14. The polypeptide of any preceding item, wherein the polypeptide is isolated.

15. The polypeptide of any preceding item, wherein the polypeptide is non-natural and/or a recombinant polypeptide.

16. The polypeptide of any preceding item, wherein the amino acid sequence is not polypeptide T310_0455 from the strain deposited under CBS 394.64, which has lysozyme activity.

17. The polypeptide of any preceding item, having a molecular weight between 10 and 5 kilo Daltons.

18. The polypeptide of any preceding item, having an isoelectric point between 2 and 7.

19. The polypeptide of any preceding item, having a pH optimum between 3 and 7.

20. The polypeptide of any preceding item, having a temperature optimum between 40 and 80 degrees Celsius.

21. The polypeptide of any preceding item, wherein the polypeptide is a recombinant polypeptide.

22. The polypeptide of any preceding item, wherein the polypeptide is a naturally occurring polypeptide.

23. The polypeptide of any preceding item, wherein the polypeptide is isolated.

24. A polypeptide comprising the polypeptide of items 1 to 23 bound to one or more additional moieties.

25. The polypeptide of item 24, comprising one or more additional polypeptides covalently bound at the N-terminus and/or the C-terminus of the one or more additional polypeptides to the N-terminus and/or the C-terminus of the polypeptide of items 1 to 23.

26. The polypeptide of item 24, wherein the moiety is a glycosyl moiety.

27. The polypeptide of item 26, wherein the glycosyl moiety is [typical glycosylation for *Rasamsonia*, if any].

28. The polypeptide of item 24, wherein the glycosyl moiety is a polyethylene glycol (PEG) moiety.

29. The polypeptide of item 28, wherein the PEG moiety is linear or branched or a combination thereof.

30. The polypeptide of items 29, wherein polyethylene glycol is attached in an amount sufficient to make the protein less immunogenic and/or antigenic and/or to increase the half-life of the polypeptide in a human or animal.

31. The polypeptide of item 24 to 30, having improved binding and/or improved solubility and/or improved enzyme activity of the hybrid polypeptide compared to the polypeptide of items 1 to 23.

32. The polypeptide of items 24 to 30, wherein the polypeptide comprise a protective agent reversibly attached to or near the active site of the polypeptide.

33. The polypeptide of item 32, wherein the protective agent is a monomer or polymer of glucosamine.

34. The polypeptide of item 33, wherein the glucosamine is selected from the group consisting of tetraglucosamine and heptaglucosamine.

35. A polynucleotide encoding the polypeptide of any preceding items or genomic DNA thereof.

36. The polynucleotide of item 35, comprising a nucleic acid sequence having at least 70%, such as at least 80%, such as at least 85%, a such as at least 90%, such as at least 91%, such as at least 92%, such as at least 93%, such as at least 94%, such as at least 95%, at least such as 96%, such as at least 97%, such as at least 98%, such as at least 99%, such as at least 99.25, such as at least 99.50, such as at least 99.75% identity to the SEQ ID NO:1 or genomic DNA thereof.

37. The polynucleotide of item 36, comprising SEQ ID NO:1 or genomic DNA thereof.

38. The polynucleotide of item 37, comprising the nucleotide sequence comprised in SEQ ID NO:1 encoding the mature polypeptide of SEQ ID NO:2.

39. The polynucleotide of item 38 consisting of nucleotides 55 to 837 of SEQ ID NO: 1

40. The polynucleotide of item 35, wherein the sequence hybridizes under stringency conditions selected from low stringency conditions, medium to low stringency conditions, medium stringency conditions, medium to high stringency conditions, high stringency conditions or very high stringency conditions with the complement to the nucleotide sequence of SEQ ID NO:1 or genomic DNA thereof.

41. The polynucleotide of item 40, wherein the sequence hybridizes with the complement to the nucleotide sequence comprised in SEQ ID NO:1 encoding the mature polypeptide of SEQ ID NO:2 or genomic DNA thereof.

42. The polynucleotide of item 41, wherein the sequence hybridizes with the complement to nucleotides 55-837 of SEQ ID NO:1 or genomic DNA thereof.

43. The polynucleotide of any preceding item, wherein the polynucleotide is a functional polynucleotide variant.

44. A nucleic acid construct comprising the polynucleotide of items 35 to 43 wherein the polynucleotide is operably linked to one or more control sequences which direct the expression of a polypeptide from the polynucleotide in a microbial cell harboring the nucleic acid construct.

45. An expression vector comprising a polynucleotide of items 35 to 43, a promoter sequence and transcriptional and translational stop signals.

46. A host cell comprising the polypeptide of items 1 to 34, the polynucleotide of items 35 to 43 or the nucleic acid construct of item 44 or the vector of item 45.

47. The host cell of item 46, wherein the cell is an isolated wild type cell.

48. The host cell of item 46, wherein the cell is an isolated recombinant cell.

49. The host cell of items 46 to 48, wherein the cell is a fungus or a yeast.

50. The host cell of items 49, wherein the fungus is a filamentous fungus.

51. The host cell of items 50, wherein the fungus is selected from the group consisting of the genera *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Rasamsonia, Thermoascus, Thielavia, Tolypocladium* and *Trichoderma*.

52. The host cell of items 49, wherein the yeast is *Pichia*.

53. The host cell of items 46 to 52, wherein one or more genes have been deleted, knocked-out or disrupted in full or in part.

54. A transgenic plant, plant part or plant cell comprising the polypeptide, the polynucleotide and/or the nucleic acid construct and/or vector of any preceding item.

55. A composition comprising the polypeptide of items 1 to 34 and/or the cell of items 46 to 53.

56. The composition of item 55, further comprising one or more additional compounds selected from [list of relevant compounds depending on application].

57. The composition of items 55 to 56, wherein the composition is in a dry form such as a spray dried, spray cooled, lyophilized, flash frozen, granular, microgranular, capsule or microcapsule form.

58. The composition of items 55 to 57, wherein the composition is in a liquid form such as such as a stabilized liquid comprising one or more stabilizers selected from sugars, polyols and organic acid.

59. A pharmaceutical composition comprising the polypeptide of items 1 to 34 and a pharmaceutically acceptable vehicle, carrier or excipient.

60. A detergent composition comprising the polypeptide of items 1 to 34 and a surfactant.

61. A food composition comprising the polypeptide of items 1 to 34 and a nutrient suitable for human consumption.

62. A feed composition comprising the polypeptide of items 1 to 34 and a nutrient suitable for animal consumption.

63. A dentifrice composition comprising the polypeptide of items 1 to 34 and a cleansing agent suitable for oral use in a mammal.

64. A cosmetic composition comprising the polypeptide of items 1 to 34 and a cleansing agent suitable for topical use on a mammal.

65. A method for preparing a polypeptide of items 1 to 34 comprising cultivating a host cell of items 46 to 53 under condition allowing the host cell to express the polypeptide and, optionally, recovering the expressed polypeptide.

66. A method for preparing host cells of items 46 to 53, comprising selecting one or more host cells of items 46 to 53 and propagating them under conditions suitable for the cells to multiply and, optionally, isolating the host cells.

67. A method for reducing immunogenicity of the polypeptide of items 1 to 34 comprising binding one or more PEG moieties to the polypeptide.

68. Non-therapeutic use of a polypeptide according to any of the items 1 to 34 for treating a peptidoglycan or chitodextrin substrate.

69. Non-therapeutic use of a polypeptide according to any of the items 1 to 34 for killing or inhibiting a microorganism.

70. Use of a polypeptide according to items 68 or 69 for removing and/or inhibiting biofilm or killing and/or inhibiting a microorganism forming biofilm.

71. Use of a polypeptide according to item 69 for killing and/or inhibiting a microorganism in food composition.

72. The use of item 71, wherein the food composition comprise material of animal origin.

73. The use of item 72, wherein the material of animal origin is meat.

74. Use of a polypeptide according to item 69 for killing and/or inhibiting a microorganism in a food processing facility.

75. The use of item 74, wherein the food processing facility is a meat processing facility, a milk processing facility or a food cooking facility.

76. Use of a polypeptide according to item 69 for killing and/or inhibiting a microorganism in an animal feed composition.

77. The use of item 76, wherein the animal feed composition comprise material of animal origin.

78. The use of item 77, wherein the material of animal origin is meat.

79. Use of a polypeptide according to item 69 for killing and/or inhibiting a microorganism in an animal feed processing facility.

80. Use of a polypeptide according to item 69 for killing and/or inhibiting a microorganism in an agricultural facility.

81. Use of a polypeptide according to item 69 for killing and/or inhibiting a microorganism in a household facility.

82. The use of item 81, wherein the household facility is selected from laundry and dishes.

83. Use of a polypeptide according to item 69 for killing and/or inhibiting a microorganism in a hospital facility.

84. The use of item 83, wherein the hospital facility is a clinical or surgical instrument, a medical device and/or an implant.

85. Use of a polypeptide according to item 69 for killing and/or inhibiting a microorganism in a fermentation facility.

86. The polypeptide of items 1 to 34 or the host cell of items 47 to 53 or the composition of items 55 to 59 for killing and/or inhibiting a microorganism on or in a human or animal subject.

87. The polypeptide of items 1 to 34 or the host cell of items 47 to 53 or the composition of items 55 to 59 for treating and/or preventing an infectious disease on or in a human or animal subject.

88. Use of the polypeptide of items 1 to 34 or the host cell of items 47 to 53 or the composition of items 55 to 59 for the preparation of a medicament for killing and/or inhibiting a microorganism on or in a human or animal subject.

89. Use of the polypeptide of items 1 to 34 or the host cell of items 47 to 53 or the composition of items 55 to 59 for the preparation of a medicament for treating and/or preventing an infectious disease on or in a human or animal subject.

90. A method for treating a peptidoglycan or chitodextrin substrate comprising contacting said substrate with an effective amount of a polypeptide of items 1 to 34.

91. A method for killing or inhibiting a microorganism comprising contacting said substrate with an effective amount of a polypeptide of items 1 to 34.

92. A method for killing and/or inhibiting a microorganism in a food composition comprising contacting the food composition with an effective amount of the polypeptide of items 1 to 34.

93. The method of item 92 wherein the food composition comprise material of animal origin.

94. The method of item 93 wherein the material of animal origin is meat.

95. A method for killing and/or inhibiting a microorganism in a food processing facility comprising contacting a food processing equipment with an effective amount of the polypeptide of items 1 to 34.

96. The method of item 95 wherein the food processing facility is a meat processing facility, a milk processing facility or a food cooking facility.
97. A method for killing and/or inhibiting a microorganism in an agricultural facility comprising contacting equipment used in an agricultural facility with an effective amount of the polypeptide of items 1 to 34.
98. A method for killing and/or inhibiting a microorganism in a household facility comprising contacting the household facility with an effective amount of the polypeptide of items 1 to 34.
99. The method of item 98 wherein the household facility is selected from laundry and dishes.
100. A method for killing and/or inhibiting a microorganism in a hospital facility comprising contacting the hospital facility with an effective amount of the polypeptide of items 1 to 34.
101. The method of item 100 wherein the hospital facility is selected from clinical or surgical instruments, medical devices and implants.
102. A method for killing and/or inhibiting a microorganism in a fermentation facility comprising contacting the fermentation facility with an effective amount of the polypeptide of items 1 to 34.
103. A method for killing and/or inhibiting a microorganism on or in a human or animal subject, comprising administering an effective amount of the polypeptide of items 1 to 34 or the host cell of items 47 to 53 or the composition of items 55 to 59 to the subject.
104. A method for the treating or preventing an infectious disease on or in a human or animal subject comprising administering an effective amount of the polypeptide of items 1 to 34 or the host cell of items 47 to 53 or the composition of items 55 to 59 to the subject.
105. An antibody capable of binding to one or more epitopes of the polypeptide of items 1 to 34.
106. A method for detecting the presence of a polypeptide comprising providing a sample suspected of containing the polypeptide, contacting the sample with the antibody of item 105, and detecting if binding between the antibody and a polypeptide in the sample has occurred.
107. A method for detecting the presence of an antibody comprising providing a sample suspected of containing the antibody, contacting the sample with the polypeptide of items 1 to 34, and detecting if binding between the polypeptide and the antibody in the sample has occurred.
108. A kit for detecting the polypeptide of the invention comprising a sample container, means for introducing the antibody of item 105 to the sample, and means for detecting binding of the antibody to the polypeptide in the sample.
109. A kit for detecting the antibody of the invention comprising a sample container, means for introducing the polypeptide of items 1 to 34 to the sample, and means for detecting binding of the antibody to the polypeptide in the sample.

EXAMPLES

Materials and Methods
Materials
Chemicals used in the examples herein e.g. for buffers and substrates are commercial products of at least reagent grade.
Microbial Strains
*Talaromyces emersonii* NBRC 31070 is used as source of the polypeptide of the present disclosure Media and Solutions
Cellulase expression media Aqueous solution of 1% w/v CMC, 1.5% w/v yeast extract, 0.5% w/v potassium dihydrogen phosphate, adjusted to pH 6.0
Precipitation Solution
Aqueous solution of 1M LiCl
0.7 M KCl
Aqueous solution of KCl
Lysis Buffer (L)
Aqueous solution of 25 mM Potassium Phosphate monobasic (Acros, 271080025) by adding 1.7 g of $KH_2PO_4$ to 500 ml of distilled water. Aqueous solution of 25 mM Potassium Phosphate dibasic (Acros, 10541081) by adding 0.87 g of $K_2HPO_4$ to 200 ml of distilled water. Dissolve 26.1 g of KCl in 350 ml of the 25 mM Potassium monobasic. Adjust the pH to 5.8 using the 25 mM Potassium Phosphate dibasic.
Buffer L6
Aqueous solution of Sorbitol (1 M), Tris-HCl (10 mM) and $CaCl_2.6H_2O$ (10 mM). Adjust the pH to 7.5.
Buffer L7
Aqueous solution of PEG6000 (60%), Tris-HCl (10 mM), $CaCl_2.6H_2O$) (10 mM). Adjust the pH to 7.5.
Potato Dextrose+Uridine
Aqueous solution of Potato dextrose broth and Uridine (10 mM final conc).
Regeneration Media
Aqueous solution of Sucrose (1 M), Glucose, 20× Nitrate salts, 10× Trace Elements. pH to 6.8.
1.8% Regeneration Agar (−Uridine)
Add 3.6 g of Agar to 200 ml of regeneration media.
1.8% Regeneration Agar (+Uridine)
Dissolve 0.244 g of uridine in 100 ml of regeneration media. Add 1.8 g of Agar to it.
0.7% Regeneration Agar (−Uridine)
Add 0.7 g of Agar to 100 ml of regeneration media.
0.7% Regeneration Agar (+Uridine)
Dissolve 0.244 g of uridine in 100 ml of regeneration media. Add 0.7 g of Agar to it.
Buffer 1
Aqueous solution of 30 mM Tris-HCl, 300 mM NaCl and 5 mM Imidazole adjusted to pH 7.5.
Buffer 2
Aqueous solution of 30 mM Tris-HCl 300 mM NaCl 10 mM Imidazole, adjusted to pH 7.5
Buffer 3
Aqueous solution of 30 mM Tris-HCl, 300 mM NaCl, 200 mM Imidazole, adjusted to pH 7.5
Buffer 4
Aqueous solution of 100 mM Na Acetate adjusted to pH 5.0
Buffer 5
Aqueous solution of 1M Tris-HCl adjusted to pH 7.5
Buffer 6
Aqueous solution of 300 mM NaCl, 10 mM Imidazole, adjusted to pH 7.5
Buffer 7
Aqueous solution of 50 mM Sodium phosphate, 300 mM NaCl adjusted to pH 7.5.
Buffer 8
Aqueous solution of 50 mM Sodium phosphate, 300 mM NaCl, 300 mM Imidazole adjusted to pH 7.5.
Buffer A
Aqueous solution of 50 mM Na Phosphate, 1.2 M Ammonium sulfate adjusted to pH 7.0.

Buffer B

Aqueous solution of 50 mM Na Phosphate adjusted to pH 7.0.

Lysozyme Fluorescence Substrate Buffer

Aqueous solution of 0.1 M Na acetate, 0.1 M NaCl, 5 mM CaCl adjusted to pH 5.0.

Lysozyme Cell Lysis Substrate Buffer

Aqueous solution of 0.1 M Na acetate adjusted to pH 5.0

Lysozyme Cell Lysis Osmolarity Buffer

Aqueous solution of 0.7 M Na acetate adjusted to pH 5.0

Lysozyme Fluorescence Substrate Solution

Fluorescein labelled *Micrococcus* lysodeikticus cell wall material is dissolved in Lysozyme substrate buffer to prepare a 1 mg/ml stock solution. Final substrate solution is made by freshly preparing a 1:20 dilution with Lysozyme substrate buffer.

Lysozyme Cell Lysis Substrate Solution

*Micrococcus* lysodeikticus ATCC No. 4698 cell suspensions are prepared by dissolving 45 mg of freeze-dried cells in 50 ml 0.1 M Na acetate pH 5.0.

YPD Medium

Aqueous solution of 10 g/l yeast extract (Biokar, A1 202HA); 20 g/l peptone (Biokar, A1601 HA) and 20 g/l agar (Sigma Aldrich 05040).

BMGY medium

Aqueous solution of 10 g/l yeast extract (Biokar, A1 202HA); 20 g/l peptone (Biokar, A1601 HA); 100 mM potassium phosphate pH 6.0; 1× yeast nitrogen base; 1× biotin and 1× glycerol.

Potassium Phosphate Buffer pH 6.0

Aqueous solution of Potassium phosphate monobasic (Acros, 271080025) and Potassium phosphate dibasic (Acros, 10541081).

10× Yeast Nitrogen Base

Aqueous solution of 34 g/L Yeast nitrogen base without amminoacids (Sigma, Y0626) and 100 g/L ammonium sulfate (Fisher, A644065)

500× Biotin

Aqueous solution of 0.2 g/L biotin (Sigma Aldrich, B4639)

10× Glycerol

Aqueous solution of 10% (v/v) glycerol (Fisher, G065017)

BMMY Medium

Aqueous solution of 10 g/l yeast extract (Biokar, A1 202HA); 20 g/l peptone (Biokar, A1601 HA); 100 mM potassium phosphate buffer pH 6.0; 1× yeast nitrogen base 1× biotin and 1× methanol.

10× Methanol:

Aqueous solution of 5% (v/v) methanol (Sigma Aldrich, 32213)

Lysozyme Fluorescence Activity Assay

Lysozyme activity of a sample is measured by 1) preparing a sample solutions (S) by mixing 50 µl lysozyme substrate solution with 50 µl sample in triplicate,
2) preparing first control solutions (C1) by mixing 50 µl lysozyme buffer solution with 50 µl sample in triplicate,
3) preparing a second control solutions (C2) by mixing 50 µl lysozyme substrate solution with 50 µl lysozyme buffer solution in triplicate.

The mixtures are incubated at 60° C. for 24 hours and fluorescence is measured using a Qubit 2.0 raw mode blue detector. After reading 20 µl of buffer 5 is added to each mixture and mixed by vortex. The mixtures are the incubated for 5 min. at 60° C. and fluorescence is measured again using the Qubit 2.0 raw mode blue detector.

Lysozyme Cell Lysis Assay of SEQ ID NO: 2

Cell lysis of a sample is measured by 1) preparing a sample solutions (S) by mixing 200 µl *Micrococcus* lysodeikticus cell suspension, 520 µl Lysozyme cell lysis substrate buffer, 80 µl Lysozyme cell lysis osmolarity buffer with 200 µl sample in triplicate,
2) preparing first control solutions (C1) by mixing 200 µl *Micrococcus* lysodeikticus cell suspension, 520 µl Lysozyme cell lysis substrate buffer, 80 µl Lysozyme cell lysis osmolarity buffer with 200 µl sample in triplicate,
3) preparing a second control solutions (C2) by mixing 200 µl *Micrococcus* lysodeikticus cell suspension, 520 µl Lysozyme cell lysis substrate buffer, 80 µl Lysozyme cell lysis osmolarity buffer with 200 µl sample in triplicate.

The mixtures are incubated at 50° C. with shaking at 800 rpm in Thermomixer C for 15 hours and 21 hours and absorbance change is measured using a Multiskan GO in cuvette reading mode.

Lysozyme Cell Lysis Assay of Purified *R. emersonii* Lysozyme

Cell lysis of a sample is measured by 1) preparing a sample solutions (S) by mixing 200 µl *Micrococcus* lysodeikticus cell suspension, 520 µl Lysozyme cell lysis substrate buffer, 80 µl Lysozyme cell lysis osmolarity buffer with 200 µl sample in triplicate,
2) preparing first control solutions (C1) by mixing 200 µl *Micrococcus* lysodeikticus cell suspension, 520 µl Lysozyme cell lysis substrate buffer, 80 µl Lysozyme cell lysis osmolarity buffer with 200 µl sample in triplicate, The mixtures are incubated at 50° C. with shaking at 800 rpm in Thermomixer C for 13.5 hours 18.5 hours and 23 hours and absorbance change is measured using a Multiskan GO in cuvette reading mode.

Example 1 Gene Isolation and Sequencing

*Talaromyces emersonii* NBRC 31070 is grown in a 250 ml conical flask with 100 ml of cellulase expression media for 3 days at 45° C. at 180 rpm. Biomass is harvested by filtration with sterile Miracloth. Frozen biomass is grinded under liquid nitrogen and then used to extract RNA using the RNeasy Plant Mini Kit (Qiagen). RNA is cleaned using a precipitation solution and cDNA therefrom prepared using the Iscript cDNA Synthesis kit from Biorad. Using a known ATCC 16479 sequence as an indicator, two primers

```
                                        (SEQ ID NO: 3)
    F' ATGTCCGTTCGTCAGCTTCT and (SEQ ID NO: 4)
    R' CTAATTGTTATCAAGGGTGCAGGT
``` are designed to amplify the homologous gene from the NBRC 31070 cDNA.

The gene is amplified from cDNA using Herculase II DNA polymerase from Agilent and subcloned into the pJET1.2 cloning vector using the CloneJET PCR cloning kit from ThermoFisher. The gene is then sequenced in triplicate using standard sequence methodology (SEQ ID NO 1).

Example 2 Gene Cloning

Two Primers

```
F':
                                    (SEQ ID NO: 5)
AAAAGAATTCTTGCCTTTCCCCCAGCCT
and R':
                                    (SEQ ID NO: 6)
AAAAATCTAGACCATTGTTATCAAGGGTGCAGGT
``` are designed to amplify the gene minus the signal peptide and minus the stop codon which is inserted into an expression vector for *Pichia pastoris* containing the alpha factor signal sequence, KEX2 cleavage site and a C-terminal His-tag.

For *Pichia pastoris*, the construct is ligated into a pPICZαA plasmid and transformed into Top10F' Chemically Competent *E. coli* (ThermoFisher) and the sequence further verified by sequencing amplification.

After verification the plasmid construct is transformed into *P. pastoris* X33 (Invitrogen) and colonies selected for on YPD Zeocin plates. Six transformants are grown in 25 ml BMGY medium in a 250 ml baffled flask at 30° C. and 250 rpm until the cultures reach an OD of 2-6. The cells are harvested by centrifugation and used to inoculate 100 ml of BMMY medium in a 1 L baffled flask. Protein expression is induced with the addition of 0.5% methanol every 24 hours. Cultures are harvested after 96 hours of induction and biomass is removed by centrifugation. Protein is analyzed by SDS-PAGE (4-15% gradient gel, BioRad). The clone producing the highest concentration of protein is selected for protein expression and purification. Image of the SDS-PAGE gel is shown in FIG. 1.

For *Aspergillus awamori* the construct is ligated into an ANIp7 plasmid and transformed into Top10F' Chemically Competent *E. coli* (ThermoFisher) and the sequence further verified by sequencing amplification.

After verification the plasmid construct is transformed into *A. awamori* using the PEG/CaCl$_2$) method and colonies selected for on regeneration agar plates. Ten Transformants are grown in 24-well plates (10 ml well volume) containing 4 ml of minimal media (MMJ) (12% D-Maltose, 200 ml of 4× Nitrate salt stock solution, 45 mM MgSO4, 4× of Hunter Trace Element). The clone producing the highest concentration of protein is selected for protein expression and purification.

Image of the SDS-PAGE gel is shown in FIG. 2.

Example 3 Protein Expression

A clone of *Pichia pastoris* of example 2 (X33_10_Te1_008550) is grown in 150 mL BMMY medium in a 1 L baffled flask by seeding the flask with inoculum culture to OD 1. *Pichia p.* is then grown over 96 hours at 30° C. 220 rpm. His-tagged protein expression (His-tagged lysozyme of the invention) is induced by addition of methanol at 0.5% (v/v) every 24 hours. Fermentation medium is centrifuged at 300° C. for 15 min and the supernatant is recovered for protein purification.

A clone of *Aspergillus awamori* of example 2 (Aw_6_Te1_008500) is grown in 500 ml shake flasks in minimal media (MMJ) (12% maltodextrin, 4× Nitrate salt solutions, 45 mM MgSO4, 4× Hunters trace elements) for 168 h at 30° C. 250 rpm for His-tagged protein expression (His-tagged lysozyme of the invention). Cultures are harvested after and biomass is removed by centrifugation. Supernatant is recovered for protein purification.

Example 4 Protein Purification

For *Pichia pastoris* the recovered supernatant of the fermentation of example 3 is filtered using a 0.2 μm PES syringe filter. The filtration step is followed by buffer exchange using 10 kDa cut off PES membrane ultra-filtration centrifuge tube. The supernatant is buffered against buffer I. Buffer exchange was confirmed by measuring pH in the filtrate flow. The retentate was pooled for Ni-affinity chromatography. Ni-NTA resin is equilibrated with buffer I and the equilibrate resin is added to the retentate fraction and mixed by inversion for 1 hour at 20 rpm at room temperature. The suspension is loaded onto a column, and the flow-through is collected. The resin is washed with two column volumes of buffer 2, and this wash step is repeated three times. Protein is eluted with one column volume of buffer 3, repeating the elution step four times. The elution fraction containing lysozyme of the invention is dialysed using 10 kDa cut-off dialysis cassette against buffer 4.

For *Aspergillus awamori*, the recovered supernatant of the fermentation of example 3 is filtered using a 0.2 μm PES filter unit. The filtered supernatant was collected for Ni-affinity chromatography. Ni-NTA resin is equilibrated with buffer 7 in the column. The supernatant is loaded onto a column, and the flow-through is collected. The resin is washed with 15 column volumes of buffer 6, and this wash step is repeated three times. Protein is eluted with one column volume of buffer 8, repeating the elution step four times. The elution fraction containing lysozyme of the invention is dialysed using 10 kDa cut-off dialysis cassette against buffer 4.

Example 5 Establishing Protein Concentration

Protein concentration of the dialysate of example 4 is determined by absorbance at 280 nm. Extinction coefficient for the His-tagged lysozyme of the invention is determined by Protparam (http://web.expasy.org/protparam/) bioinformatic software.

Example 6 Lysozyme Activity of SEQ ID NO: 2

Samples of approximately 0.5 mg/ml and 2 mg/ml of the polypeptide of the invention prepared in example 4 is tested using the lysozyme activity assay, yielding the following results.

| Sample | F T = 0 | F T = 2 | F T = 5 | F T = 10 |
|---|---|---|---|---|
| SEQ ID NO: 2 X33_10_Te1_60 0.5 mg/ml | 620.8 ± 194.6 | 2384.3 ± 71.8 | 5461.9 ± 539.3 | 6599.1 ± 481.8 |
| SEQ ID NO: 2 X33_10_Te1_60 2 mg/ml | 839.0 ± 47.9 | 5829.3 ± 241.9 | 15423.5 ± 3864.1 | 14984.2 ± 1676.6 |
| Control C1 + C2 | 956.9 ± 365.3 | 595.6 ± 77.4 | 1020.5 ± 758.7 | 865.0 ± 223.2 |

The results are further visualized in FIG. 3.

Accordingly, SEQ ID NO:2 surprisingly display a strong and significant lysozyme activity at 60° C., pH 5; which makes the polypeptide of the invention considerably acid and temperature stable.

Example 7 Cell Lysis Activity of SEQ ID NO: 2

Samples of approximately 0.01 mg/ml of the polypeptide of the invention prepared in example 4 is tested using the lysozyme cell lysis assay, yielding the following results.

| Sample | Absorbance Change T = 0 H | Absorbance Change T = 15 H | Absorbance Change T = 23 H |
|---|---|---|---|
| SEQ ID NO: 2 Aw_6_Te1_60 0.01 mg/ml | 0 ± 0.22 | 4.44 ± 1.05 | 9.48 ± 3.76 |
| Control C1 | 0 ± 0.57 | 0.60 ± 0.48 | 0.23 ± 0.47 |
| Control C2 | 0 ± 0.56 | 0.79 ± 2.11 | 0.42 ± 0.51 |

The results are further visualized in FIG. 4.

Accordingly, SEQ ID NO:2 displays significant lysis of *Micrococcus* cells at 50° C., pH 5; which makes the polypeptide of the invention considerably acid and temperature stable.

Example 8 Cell Purification of Lysozyme Peptide from Rasamsonia emersonii Culture Media The recovered supernatant of a *Rasamsonia emersonii* fermentation is concentrated 20-fold on an ultrafiltration cassette with a 10 KDa molecular weight cut-off. The concentrated supernatant is filtered using a 0.2 μm PES syringe filter. The supernatant is diluted 10-fold in buffer A. A column packed with 5 ml of Butyl Agarose resin is equilibrated with buffer A and the diluted supernatant is loaded onto the column. The resin is washed with five column volumes of buffer B. Protein is eluted with a gradient of buffer A and B. Fractions containing *Rasamsonia emersonii* lysozyme are pooled and concentrated on a centrifugal concentrator with a 3 KDa cutoff.

Example 9 Cell Lysis Activity of Rasamsonia emersonii Lysozyme Purified from Culture Media Samples of 0.03-0.013 mg/ml of *Rasamsonia emersonii* lysozyme prepared in example 9 is tested using the lysozyme cell lysis assay, yielding the following results.

| Sample | Absorbance Change T = 0 h | Absorbance Change T = 13.5 h | Absorbance Change T = 18.5 h | Absorbance Change T = 23 h |
|---|---|---|---|---|
| Purified R. emersonii lysozyme 0.013 mg/ml | 0 | 7.88 | 9.91 | 12.6 |
| Purified R. emersonii lysozyme 0.007 mg/ml | 0 | 1.85 | 4.35 | 7.53 |
| Purified R. emersonii lysozyme 0.003 mg/ml | 0 | 0.61 | 0.61 | 3.58 |
| Control C1 | 0 | 1.47 | 2.53 | 2.02 |

The results are further visualized in FIG. 5.

Purified *R. mansoni* lysozyme displays significant lysis of *Micrococcus* cells at 50° C., pH 5; in a similar manner to SEQ ID NO:2.

Example 10 Establishing Protein Concentration for Cell Lysis Activity Assays Protein concentration was estimated by measuring the absorbance shift of the dye Coomassie Brilliant Blue G-250 at 595 nm.

---

The invention claimed is:

1. An isolated, recombinant polypeptide having lysozyme activity, wherein said isolated recombinant polypeptide comprises an amino acid sequence selected from the group consisting of:
   a) a polypeptide having at least 97% amino acid sequence identity to amino acids 19 to 279 of the polypeptide set forth in SEQ ID NO: 2; and
   b) a polypeptide encoded by a polynucleotide having at least 97% nucleotide sequence identity to the nucleotides 55-837 set forth in SEQ ID NO: 1.

2. An isolated, recombinant polynucleotide encoding the isolated recombinant polypeptide of claim 1.

3. A host cell comprising:
   the isolated, recombinant polypeptide of claim 1 or the isolated, recombinant polynucleotide of claim 2.

4. A composition comprising:
   the isolated, recombinant polypeptide of claim 1 or the host cell of claim 3.

5. The composition of claim 4, wherein said composition is selected from the group consisting of:
   a) a pharmaceutical composition further comprising an acceptable vehicle, carrier or excipient;
   b) a detergent composition further comprising a surfactant;
   c) a food composition further comprising a nutrient suitable for human consumption;
   d) a feed composition further comprising a nutrient suitable for animal consumption;
   e) a dentrifice composition further comprising a cleansing agent suitable for oral use in a mammal and
   f) a cosmetic composition further comprising a cleansing agent suitable for topical use on a mammal.

6. A method for preparing the isolated, recombinant polypeptide of claim 1 comprising:
   cultivating the host cell of claim 3 under conditions allowing the host cell to express the isolated, recombinant polypeptide and, optionally, recovering the expressed isolated, recombinant polypeptide.

7. A method for preparing the host cells of claim 3, comprising selecting one or more host cells of claim 3 and propagating the host cells under conditions suitable for the host cells to multiple and, optionally, isolating the host cells.

8. A method for treating a peptidoglycan or chitodextrin substrate comprising contacting said substrate with an effective amount of the isolated, recombinant polypeptide of claim 1.

9. A method for killing or inhibiting a microorganism in a substrate or facility comprising contacting said substrate or facility with an effective amount of the isolated, recombinant polypeptide of claim 1, wherein said substrate or facility are selected from the group consisting of:
   a biofilm; a food composition; a feed composition; a food processing facility; a feed processing facility; an agricultural facility; a household facility; a hospital facility; and a fermentation facility.

10. A method for killing and/or inhibiting a microorganism on or in a human or animal subject comprising administering an effective amount of the isolated, recombinant polypeptide of claim 1 to the human or animal subject.

11. A method for treating or preventing an infectious disease on or in a human or animal subject comprising administering an effective amount of the isolated, recombinant polypeptide of claim 1 to the human or animal subject.

12. A method for killing and/or inhibiting a microorganism in a food composition comprising contacting the food composition with an effective amount of the isolated, recombinant polypeptide of claim 1.

13. The isolated, recombinant polypeptide of claim 1, wherein the isolated, recombinant polypeptide of a) has at least 99% amino acid sequence identity to the polypeptide set forth in SEQ ID NO: 1.

14. The isolated, recombinant polypeptide of claim 1, wherein the polynucleotide of b) encoding the polypeptide has at least 99% nucleotide sequence identity to the nucleotide sequence set forth in SEQ ID NO: 1.

15. The isolated, recombinant polypeptide of claim 1 consisting of an amino acid sequence selected from the group consisting of:
   a) amino acids 19 to 279 of the polypeptide set forth in SEQ ID NO: 2; and
   b) an amino acid sequence encoded by a polynucleotide having the nucleotides 55-837 set forth in SEQ ID NO: 1.

16. The isolated, recombinant polypeptide of claim 1, wherein the isolated, recombinant polypeptide has a molecular weight between 27 to 28 kilo Daltons or 27.6 kilo Daltons.

17. The isolated, recombinant polypeptide of claim 1, wherein the isolated, recombinant polypeptide has an isoelectric point between 3.5 and 4.5.

18. The isolated, recombinant polypeptide of claim 1, wherein the isolated, recombinant polypeptide has a pH optimum between 3 and 7.

19. The isolated, recombinant polypeptide of claim 1, wherein the isolated, recombinant polypeptide has a temperature optimum between 40 and 80 degrees Celsius.

20. The isolated, recombinant polypeptide of claim 1, wherein the isolated, recombinant polypeptide is bound to one or more additional moieties.

21. The isolated, recombinant polypeptide of claim 20, wherein the one or more moieties is a glycosyl moiety.

22. The isolated, recombinant polypeptide of claim 21, wherein the glycosyl moiety is a polyethylene glycol (PEG) moiety.

23. The isolated, recombinant polypeptide of claim 1, further comprising one or more additional polypeptides covalently bound at the N-terminus and/or the C-terminus of the isolated, recombinant polypeptide.

* * * * *